US010533966B2

(12) United States Patent
Huang et al.

(10) Patent No.: US 10,533,966 B2
(45) Date of Patent: Jan. 14, 2020

(54) DIGITAL TIME DOMAIN READOUT CIRCUIT FOR BIOFET SENSOR CASCADES

(71) Applicant: Taiwan Semiconductor Manufacturing Co., Ltd., Hsinchu (TW)

(72) Inventors: Yu-Jie Huang, Kaohsiung (TW); Jui-Cheng Huang, Hsinchu (TW)

(73) Assignee: Taiwan Semiconductor Manufacturing Co., Ltd. (TW)

(*) Notice: Subject to any disclaimer, the term of this patent is extended or adjusted under 35 U.S.C. 154(b) by 369 days.

(21) Appl. No.: 15/661,788

(22) Filed: Jul. 27, 2017

(65) Prior Publication Data

US 2019/0033251 A1    Jan. 31, 2019

(51) Int. Cl.
*G01N 27/414*    (2006.01)

(52) U.S. Cl.
CPC ..... *G01N 27/4145* (2013.01); *G01N 27/4148* (2013.01)

(58) Field of Classification Search
CPC .................................................... G01N 27/414
USPC .................. 204/403.01; 422/82.01–82.03
See application file for complete search history.

(56) References Cited

U.S. PATENT DOCUMENTS

| 3,449,594 | A | * | 6/1969 | Gibson | H03K 19/0948 |
| | | | | | 327/437 |
| 3,969,209 | A | * | 7/1976 | Mueller | G01N 27/48 |
| | | | | | 204/406 |
| 4,151,522 | A | * | 4/1979 | Yamauchi | G08B 29/185 |
| | | | | | 340/309.16 |
| 4,187,460 | A | * | 2/1980 | Dauge | G01R 19/252 |
| | | | | | 324/607 |
| 4,743,954 | A | * | 5/1988 | Brown | G01N 27/4148 |
| | | | | | 257/253 |
| 5,309,085 | A | * | 5/1994 | Sohn | G01N 27/4145 |
| | | | | | 257/253 |
| 5,643,742 | A | * | 7/1997 | Malin | G01N 33/5011 |
| | | | | | 324/692 |

(Continued)

FOREIGN PATENT DOCUMENTS

| CA | 2 619 000 C | 3/2017 |
| DE | 10 2007 048 727 A1 | 4/2009 |

(Continued)

OTHER PUBLICATIONS

Senillou, A. et al, Materials Science and Engineering C 1998, 6, 59-63.*

(Continued)

*Primary Examiner* — Arlen Soderquist
(74) *Attorney, Agent, or Firm* — Sterne, Kessler, Goldstein & Fox P.L.L.C.

(57) ABSTRACT

Various bioFET sensor readout circuits and their methods of operation are described. A readout circuit includes a plurality of logic gates coupled in cascade, a delay extractor, and a counting module. Each logic gate of the plurality of logic gates includes at least one bioFET sensor. The delay extractor is designed to generate a pulse-width signal based on a time difference between an output signal from the plurality of logic gates and a reference signal. The counting module is designed to receive the pulse-width signal and output a digital count corresponding to a width of the pulse-width signal.

20 Claims, 19 Drawing Sheets

(56) References Cited

U.S. PATENT DOCUMENTS

| | | | |
|---|---|---|---|
| 5,980,708 A * | 11/1999 | Champagne | G01N 27/48 204/400 |
| 5,990,709 A * | 11/1999 | Thewes | G06F 7/53 327/89 |
| 6,313,621 B1 * | 11/2001 | Zwack | G01R 25/005 324/76.52 |
| 6,333,645 B1 * | 12/2001 | Kanetani | H03K 19/1738 326/98 |
| 6,742,133 B2 | 5/2004 | Saeki | |
| 7,280,069 B2 | 10/2007 | Honya et al. | |
| 7,794,658 B2 * | 9/2010 | Kermani | G01N 27/3273 422/82.01 |
| 8,224,604 B1 * | 7/2012 | Amrutur | G01R 31/3016 327/153 |
| 2002/0049389 A1 * | 4/2002 | Abreu | A61B 3/1241 600/558 |
| 2003/0219824 A1 * | 11/2003 | Malin | B01J 19/0046 435/7.1 |
| 2005/0191683 A1 | 9/2005 | Yoo et al. | |
| 2006/0076973 A1 * | 4/2006 | Furukawa | G01R 31/31928 324/762.02 |
| 2006/0109046 A1 * | 5/2006 | Huang | H03K 3/00 327/365 |
| 2006/0147983 A1 * | 7/2006 | O'uchi | G01N 27/4145 435/29 |
| 2009/0237534 A1 | 9/2009 | Okumura | |
| 2011/0080200 A1 | 4/2011 | Zhou | |
| 2011/0276278 A1 * | 11/2011 | Ishige | G01N 27/3272 702/25 |
| 2012/0173159 A1 * | 7/2012 | Davey | G16B 30/00 702/20 |
| 2013/0065257 A1 * | 3/2013 | Wang | C12Q 1/001 435/7.92 |
| 2013/0071839 A1 * | 3/2013 | Seelig | C12Q 1/6876 435/6.11 |
| 2013/0200438 A1 | 8/2013 | Liu et al. | |
| 2014/0308752 A1 | 10/2014 | Chang et al. | |
| 2015/0042380 A1 * | 2/2015 | Manning | G11C 7/06 326/38 |
| 2015/0053925 A1 | 2/2015 | Liu et al. | |
| 2015/0084099 A1 | 3/2015 | Shen et al. | |
| 2015/0195470 A1 | 7/2015 | Millet et al. | |
| 2015/0233864 A1 | 8/2015 | Shen et al. | |
| 2017/0067890 A1 | 3/2017 | Lin et al. | |
| 2017/0160226 A1 | 6/2017 | Huang et al. | |

FOREIGN PATENT DOCUMENTS

| | | |
|---|---|---|
| DE | 10 2016 117 555 A1 | 6/2017 |
| KR | 10-1995-0013062 B1 | 5/1995 |
| KR | 10-1096102 B1 | 12/2011 |

OTHER PUBLICATIONS

Senillou, A. et al, Talanta 1999, 50, 219-226.*
Hara, M. et al, Biosensors & Bioelectronics 2002, 17, 173-179.*
Ghallab, Y. H. et al, Proceedings of the International Conference on MEMS, NANO and Smart Systems 2003, 255-258.*
Chunhua, W. et al, APCCAS 2008—2008 IEEE Asia Pacific Conference on Circuits and Systems 2008, 407-410.*
Beckett, P., SPIE 2008, 7268, paper 72680E, 12 pages.*
Ohno, Y. et al, Nano Letters 2009, 9, 3318-3322.*
Wong Jr, W. et al, Electronics Letters 2010, 46, 331-332.*
Chan, W. P. et al, IEEE Journal of Solid-State Circuits 2010, 45, 1923-1934.*
Gardner, J. W. et al, IEEE Sensors Journal 2010, 10, 1833-1848.*
Kergoat, L. et al, Analytical and Bioanalytical Chemistry 2012, 402, 1813, 1826.*
Aljada, M. et al, Journal of Physics D: Applied Physics 2012, 45, paper 225105, 7 pages.*
Sohbati, M. et al, 2013 IEEE Biomedical Circuits and Systems Conference (BioCAS) 2013, 37-40.*
Duan, X. et al, Nanomedicine 2013, 8, 1839-1851.*
Huang, J.-C. et al, 2015 IEEE International Electron Devices Meeting (IEDM) 2015, 29.2.1-29.2.4.*
Pachauri, V. et al, Essays in Biochemistry 2016, 60, 81-90.*
Priydarshi, A. et al, Journal of Physics: Conference Series 2016, 755, paper 012055, 9 pages.*
Shadman, A. et al, Superlattices and Microstructures 2017, 111, 414-422.*

* cited by examiner

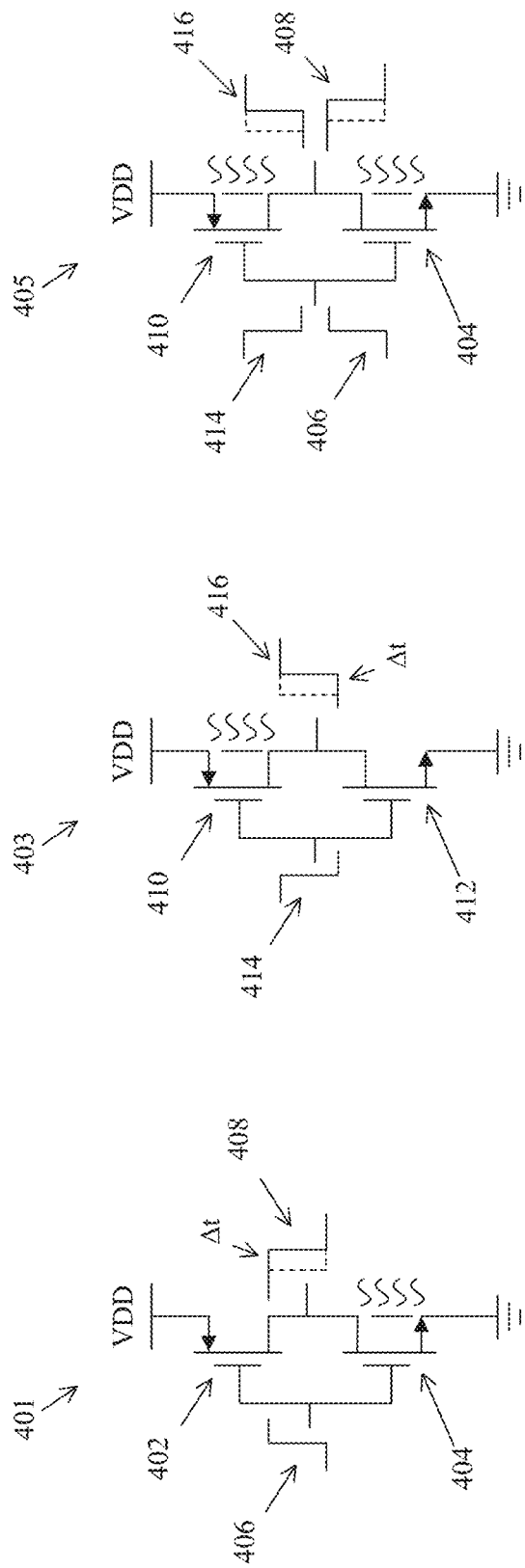

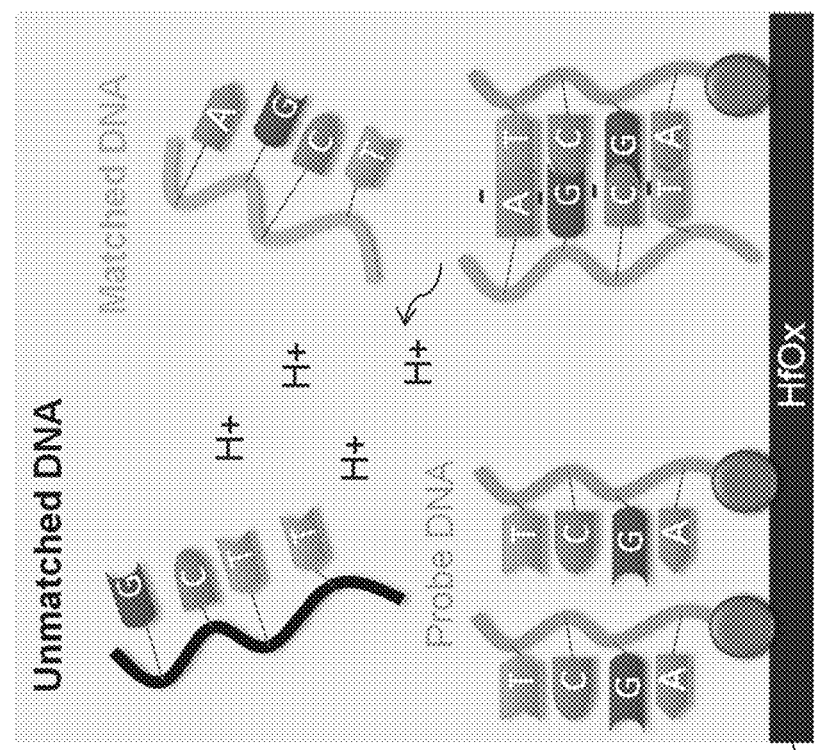
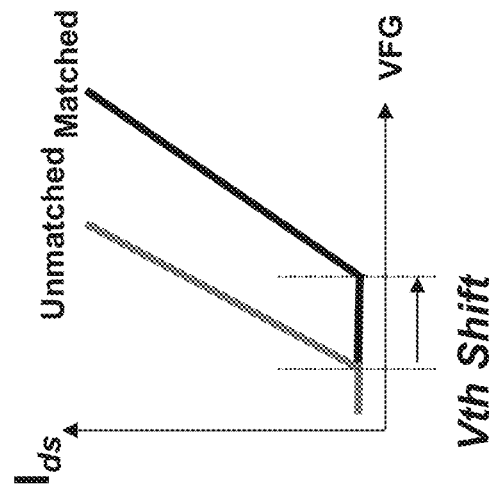
FIG. 16A
FIG. 16B

DIGITAL TIME DOMAIN READOUT CIRCUIT FOR BIOFET SENSOR CASCADES

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

Additional circuitry is often required to read out signals from the biosensors and produce a quantifiable detection signal. Such circuitry can produce an analog output signal, or uses an analog-to-digital (ADC) converter to measure an analog signal from the biosensor and produces a digital detection signal. Analog signals are easily influenced by noise and the circuit components used with analog signals can consume a large portion of the total power of the biosensing system. Furthermore, integrating an ADC increases the chip cost and the die area.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 4A-4C illustrate logic gates incorporating a bioFET sensor, according to some embodiments.

FIG. 16A illustrates binding mechanics of DNA on a receptor surface, according to some embodiments.

FIG. 16B illustrates a change in threshold voltage for the exemplary dual gate back-side sensing bioFET based on matched analyte binding, according to some embodiments.

DETAILED DESCRIPTION

Figure 1:
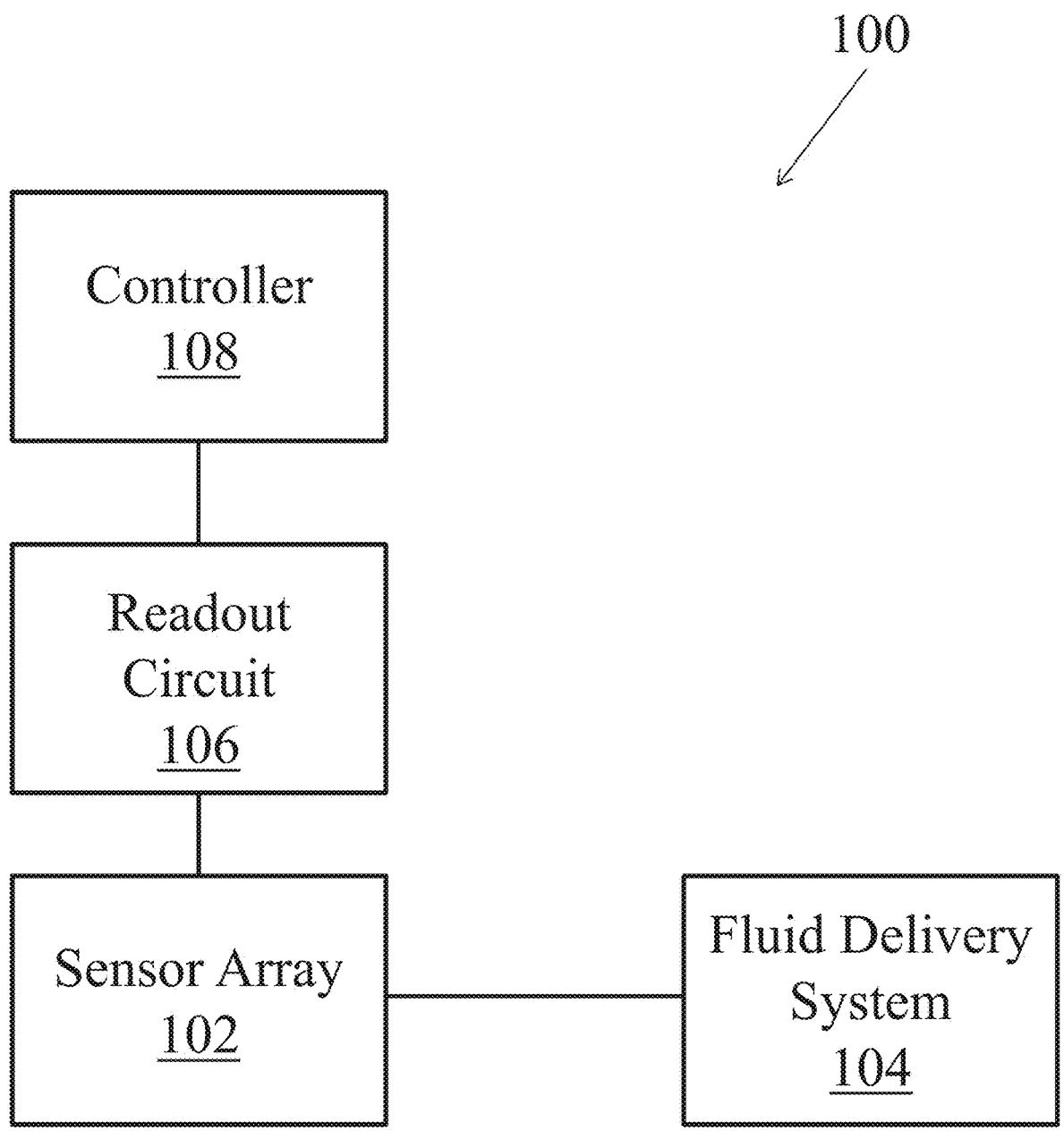
FIG. 1 illustrates components of a sensing device, according to some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include embodiments in which the first and second features are formed in direct contact, and may also include embodiments in which additional features may be formed and/or disposed between the first and second features, such that the first and second features may not be in direct contact. In addition, the present disclosure may repeat reference numerals and/or letters in the various examples. This does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (e.g., rotated 90 degrees or at other orientations) and the spatially relative descriptors used herein may likewise be interpreted accordingly.

Terminology

Unless defined otherwise, the technical and scientific terms used herein have the same meanings as commonly understood by one of ordinary skill in the art to which this disclosure belongs. Although any methods and materials similar or equivalent to those described herein can be used in the practice or testing of embodiments in accordance with the disclosure; the methods, devices, and materials are now described. All patents and publications mentioned herein are incorporated herein by reference for the purpose of describing and disclosing the materials and methodologies which are reported in the publications which might be used in connection with the present disclosure.

The acronym "FET," as used herein, refers to a field effect transistor. An example of a type of FET is referred to as a metal oxide semiconductor field effect transistor (MOSFET). Historically, MOSFETs have been planar structures built in and on the planar surface of a substrate such as a semiconductor wafer. But recent advances in semiconductor manufacturing have resulted in three-dimensional, fin-based MOSFET structures.

The term "bioFET" refers to a FET that includes a layer of immobilized capture reagents that act as surface receptors to detect the presence of a target analyte of biological origin. A bioFET is a field-effect sensor with a semiconductor transducer, according to some embodiments. One advantage of bioFETs is the prospect of label-free operation. Specifically, bioFETs enable the avoidance of costly and time-consuming labeling operations such as the labeling of an analyte with, for instance, fluorescent or radioactive probes. The analytes for detection by a BioFET will normally be of biological origin, such as—without limitation—proteins, carbohydrates, lipids, tissue fragments, or portions thereof. A BioFET can be part of a broader genus of FET sensors that may also detect any chemical compound (known in the art as a "ChemFET") or any other element, including ions, such as protons or metallic ions (known in the art as an "ISFET"). This disclosure applies to all types of FET-based sensors ("FET sensor"). One specific type of FET sensor herein is a Dual-Gate Back Side Sensing FET Sensor.

"S/D" refers to the source/drain junctions that form two of the four terminals of a FET.

The expression "high-k" refers to a high dielectric constant. In the field of semiconductor device structures and manufacturing processes, high-k refers to a dielectric constant that is greater than the dielectric constant of $SiO_2$ (i.e., greater than 3.9).

The term "analysis" generally refers to a process or step involving physical, chemical, biochemical, or biological analysis that includes, but is not limited to, characterization, testing, measurement, optimization, separation, synthesis, addition, filtration, dissolution, or mixing.

The term "assay" generally refers to a process or step involving the analysis of a chemical or a target analyte and includes, but is not limited to, cell-based assays, biochemical assays, high-throughput assays and screening, diagnostic assays, pH determination, nucleic acid hybridization assays, polymerase activity assays, nucleic acid and protein sequencing, immunoassays (e.g., antibody-antigen binding assays, ELISAs, and iqPCR), bisulfite methylation assays for detecting methylation pattern of genes, protein assays, protein binding assays (e.g., protein-protein, protein-nucleic acid, and protein-ligand binding assays), enzymatic assays, coupled enzymatic assays, kinetic measurements (e.g., kinetics of protein folding and enzymatic reaction kinetics), enzyme inhibitor and activator screening, chemiluminescence and electrochemiluminescence assays, fluorescent assays, fluorescence polarization and anisotropy assays, absorbance and colorimetric assays (e.g., Bradford assay, Lowry assay, Hartree-Lowry assay, Biuret assay, and BCA assay), chemical assays (e.g., for the detection of environmental pollutants and contaminants, nanoparticles, or polymers), and drug discovery assays. The apparatus, systems, and methods described herein may use or adopt one or more of these assays to be used with the FET sensor designs described herein.

The term "liquid biopsy" generally refers to a biopsy sample obtained from a subject's bodily fluid as compared to a subject's tissue sample. The ability to perform assays using a body fluid sample is oftentimes more desirable than using a tissue sample. The less invasive approach using a body fluid sample has wide ranging implications in terms of patient welfare, the ability to conduct longitudinal disease monitoring, and the ability to obtain expression profiles even when tissue cells are not easily accessible, e.g., in the prostate gland. Assays used to detect target analytes in liquid biopsy samples include, but are not limited to, those described above. As a non-limiting example, a circulating tumor cell (CTC) assay can be conducted on a liquid biopsy sample.

For example, a capture reagent (e.g., an antibody) immobilized on a FET sensor may be used for detection of a target analyte (e.g., a tumor cell marker) in a liquid biopsy sample using a CTC assay. CTCs are cells that have shed into the vasculature from a tumor and circulate, e.g., in the bloodstream. Generally, CTCs are present in circulation in extremely low concentrations. To assay the CTCs, CTCs are enriched from patient blood or plasma by various techniques known in the art. CTCs may be stained for specific markers using methods known in the art including, but not limited to, cytometry (e.g., flow cytometry)-based methods and immunohistochemistry (IHC)-based methods. For the apparatus, systems, and methods described herein, CTCs may be captured or detected using a capture reagent. In another example, the nucleic acids, proteins, or other cellular milieu from the CTCs may be targeted as target analytes for binding to, or detection by, a capture reagent.

An increase in target analyte expressing or containing CTCs may help identify the subject as having a cancer that is likely to respond to a specific therapy (e.g., one associated with the target analyte) or allow for optimization of a therapeutic regimen with, e.g., an antibody to the target analyte. CTC measurement and quantitation can provide information on, e.g., the stage of tumor, response to therapy, disease progression, or a combination thereof. The information obtained from detecting the target analyte on the CTC can be used, e.g., as a prognostic, predictive, or pharmacodynamic biomarker. In addition, CTCs assays for a liquid biopsy sample may be used either alone or in combination with additional tumor marker analysis of solid biopsy samples.

The term "identification" generally refers to the process of determining the identity of a target analyte based on its binding to a capture reagent whose identity is known.

The term "measurement" generally refers to the process of determining the amount, quantity, quality, or property of a target analyte based on its binding to a capture reagent.

The term "quantitation" generally refers to the process of determining the quantity or concentration of a target analyte based on its binding to a capture reagent.

The term "detection" generally refers to the process of determining the presence or absence of a target analyte based on its binding to a capture reagent. Detection includes but is not limited to identification, measurement, and quantitation.

The term "chemical" refers to a substance, compound, mixture, solution, emulsion, dispersion, molecule, ion, dimer, macromolecule such as a polymer or protein, biomolecule, precipitate, crystal, chemical moiety or group, particle, nanoparticle, reagent, reaction product, solvent, or fluid any one of which may exist in the solid, liquid, or gaseous state, and which is typically the subject of an analysis.

The term "reaction" refers to a physical, chemical, biochemical, or biological transformation that involves at least one chemical and that generally involves (in the case of chemical, biochemical, and biological transformations) the breaking or formation of one or more bonds such as covalent, noncovalent, van der Waals, hydrogen, or ionic bonds. The term "reaction" includes chemical reactions such as synthesis reactions, neutralization reactions, decomposition reactions, displacement reactions, reduction-oxidation reactions, precipitation, crystallization, combustion reactions, and polymerization reactions, as well as covalent and non-covalent binding, phase change, color change, phase formation, crystallization, dissolution, light emission, changes of light absorption or emissive properties, temperature change or heat absorption or emission, conformational change, and folding or unfolding of a macromolecule such as a protein.

"Capture reagent," as used herein, is a molecule or compound capable of binding the target analyte or target reagent, which can be directly or indirectly attached to a substantially solid material. The capture agent can be a chemical, and specifically any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte," as used herein, is the substance to be detected in the test sample using the present disclosure. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Test sample," as used herein, means the composition, solution, substance, gas, or liquid containing the target analyte to be detected and assayed using the present disclosure. The test sample can contain other components besides the target analyte, can have the physical attributes of a liquid, or a gas, and can be of any size or volume, including for example, a moving stream of liquid or gas. The test sample can contain any substances other than the target analyte as long as the other substances do not interfere with the binding of the target analyte with the capture reagent or the specific binding of the first binding member to the second binding member. Examples of test samples include, but are not limited to, naturally-occurring and non-naturally occurring samples or combinations thereof. Naturally-occurring test samples can be synthetic or synthesized. Naturally-occurring test samples include body or bodily fluids isolated from anywhere in or on the body of a subject, including but not limited to, blood, plasma, serum, urine, saliva or sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof, and environmental samples such as ground water or waste water, soil extracts, air, and pesticide residues or food-related samples.

Detected substances can include, e.g., nucleic acids (including DNA and RNA), hormones, different pathogens (including a biological agent that causes disease or illness to its host, such as a virus (e.g., H7N9 or HIV), a protozoan (e.g., Plasmodium-causing malaria), or a bacteria (e.g., *E. coli* or *Mycobacterium tuberculosis*)), proteins, antibodies, various drugs or therapeutics or other chemical or biological substances, including hydrogen or other ions, non-ionic molecules or compounds, polysaccharides, small chemical compounds such as chemical combinatorial library members, and the like. Detected or determined parameters may include, but are not limited to pH changes, lactose changes, changing concentration, particles per unit time where a fluid flows over the device for a period of time to detect particles (e.g., particles that are sparse), and other parameters.

As used herein, the term "immobilized," when used with respect to, e.g., a capture reagent, includes substantially attaching the capture reagent at a molecular level to a surface. For example, a capture reagent may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based on the properties of the substrate surface, the medium carrying the capture reagent, and the properties of the capture reagent. In some cases, a substrate surface may be first modified to have functional groups bound to the surface. The functional groups may then bind to biomolecules or biological or chemical substances to immobilize them thereon.

The term "nucleic acid" generally refers to a set of nucleotides connected to each other via phosphodiester bond and refers to a naturally occurring nucleic acid to which a naturally occurring nucleotide existing in nature is connected, such as DNA that includes deoxyribonucleotides having any of adenine, guanine, cytosine, and thymine connected to each other and/or RNA that includes ribonucleotides having any of adenine, guanine, cytosine, and uracil connected to each other. In addition, non-naturally occurring nucleotides and non-naturally occurring nucleic acids are within the scope of the nucleic acid of the present disclosure. Examples include peptide nucleic acids (PNA), peptide nucleic acids with phosphate groups (PHONA), bridged nucleic acids/locked nucleic acids (BNA/LNA), and morpholino nucleic acids. Further examples include chemically-modified nucleic acids and nucleic acid analogues, such as methylphosphonate DNA/RNA, phosphorothioate DNA/RNA, phosphoramidate DNA/RNA, and 2'-O-methyl DNA/RNA. Nucleic acids include those that may be modified. For example, a phosphoric acid group, a sugar, and/or a base in a nucleic acid may be labeled as necessary. Any substance for nucleic acid labeling known in the art can be used for labeling. Examples thereof include but are not limited to radioactive isotopes (e.g., 32P, 3H, and 14C), DIG, biotin, fluorescent dyes (e.g., FITC, Texas, cy3, cy5, cy7, FAM, HEX, VIC, JOE, Rox, TET, Bodipy493, NBD, and TAMRA), and luminescent substances (e.g., acridinium ester).

Aptamer as used herein refers to oligonucleic acids or peptide molecules that bind to a specific target molecule. The concept of using single-stranded nucleic acids (aptamers) as affinity molecules for protein binding is based on the ability of short sequences to fold, in the presence of a target, into unique, three-dimensional structures that bind the target with high affinity and specificity. Aptamers can be oligonucleotide ligands selected for high-affinity binding to molecular targets.

The term "antibody" as used herein refers to a polypeptide of the immunoglobulin family that is capable of binding a corresponding antigen non-covalently, reversibly, and in a specific manner. For example, a naturally occurring IgG antibody is a tetramer that includes at least two heavy (H) chains and two light (L) chains inter-connected by disulfide bonds. Each heavy chain includes a heavy chain variable region (abbreviated herein as "VH") and a heavy chain constant region. The heavy chain constant region includes three domains: CH1, CH2 and CH3. Each light chain includes a light chain variable region (abbreviated herein as "VL") and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The three CDRs constitute about 15-20% of the variable domains. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

The term "polymer" means any substance or compound that is composed of two or more building blocks ('mers') that are repetitively linked to each other. For example, a "dimer" is a compound in which two building blocks have been joined together. Polymers include both condensation and addition polymers. Examples of condensation polymers include polyamide, polyester, protein, wool, silk, polyurethane, cellulose, and polysiloxane. Examples of addition polymers are polyethylene, polyisobutylene, polyacrylonitrile, poly(vinyl chloride), and polystyrene. Other examples include polymers having enhanced electrical or optical properties (e.g., a nonlinear optical property) such as electroconductive or photorefractive polymers. Polymers include both linear and branched polymers.

Overview of Exemplary Biosensing Device

FIG. 1 illustrates an overview of components that may be included in a biosensor testing platform 100. Biosensor testing platform 100 includes a sensor array 102 having at least one sensing element for detecting a biological or chemical analyte and a fluid delivery system 104 designed to deliver one or more fluid samples to sensor array 102. Fluid delivery system 104 may be simple such as a microfluidic well positioned above sensor array 102 to contain a fluid over sensor array 102. Fluid delivery system 104 may also include microfluidic channels for delivering various fluids to sensor array 102. Fluid delivery system 104 may include any number of valves, pumps, chambers, channels designed to deliver fluid to sensor array 102.

A readout circuit 106 is provided to measure signals from the sensors in sensor array 102 and to generate a quantifiable sensor signal indicative of the amount of a certain analyte that is present in a target solution, according to some embodiments. Different embodiments of readout circuit 106 described herein utilize digital components to reduce power consumption and die area.

A controller 108 may be used to send and receive electrical signals to both sensor array 102 and readout circuit 106 to perform the bio or chemical sensing measurement. Controller 108 may also be used to send electrical signals to fluid delivery system 104 to, for example, actuate one or more valves, pumps, or motors.

Sensor array 102 may include an array of bioFETs, where one or more of the bioFETs in the array are functionalized to detect a particular target analyte. Different ones of the sensors may be functionalized using different capture reagents for detecting different target analytes. Further details regarding an example design of particular bioFETs are provided later.

Controller 108 may include one or more processing devices, such as a microprocessor, and may be programmable to control the operation of readout circuit 106 and/or sensor array 102. The details of controller 108 itself are not important for the understanding of the embodiments described herein. However, the various electrical signals that may be sent and received from sensor array 102 will be discussed in more detail later.

Details regarding the design and operation of the bioFET sensors themselves within sensor array 102 are provided first, followed by a detailed description of various readout circuit architectures that utilize digital components.

Dual Gate Back-Side FET Sensors

One example type of bioFET sensor that may be used in sensor array 102 is the dual gate back-side FET sensor. Dual gate back-side FET sensors utilize semiconductor manufacturing techniques and biological capture reagents to fond arrayed sensors. While MOSFETs can have a single gate electrode that is connected to a single electrical node, the dual gate back-side sensing FET sensor has two gate electrodes, each of which is connected to a different electrical node. A first one of the two gate electrodes is referred to herein as the "front-side gate" and the second one of the two gate electrodes is referred to herein as the "back-side gate." Both the front-side gate and the back-side gate are configured such that, in operation, each one may be electrically charged and/or discharged and thereby each influences the electric field between the source/drain terminals of the dual gate back-side sensing FET sensor. The front-side gate is electrically conductive, separated from a channel region by a front-side gate dielectric, and configured to be charged and discharged by an electrical circuit to which it is coupled. The back-side gate is separated from the channel region by a back-side gate dielectric and includes a bio-functionalized sensing layer disposed on the back-side gate dielectric. The amount of electric charge on the back-side gate is a function of whether a bio-recognition reaction has occurred. In the operation of dual gate back-side sensing FET sensors, the front-side gate is charged to a voltage within a predetermined range of voltages. The voltage on the front-side gate determines a corresponding conductivity of the FET sensor's channel region. A relatively small amount of change to the electric charge on the back-side gate changes the conductivity of the channel region. It is this change in conductivity that indicates a bio-recognition reaction.

One advantage of FET sensors is the prospect of label-free operation. Specifically, FET sensors enable the avoidance of costly and time-consuming labeling operations such as the labeling of an analyte with, for instance, fluorescent or radioactive probes.

Figure 2:
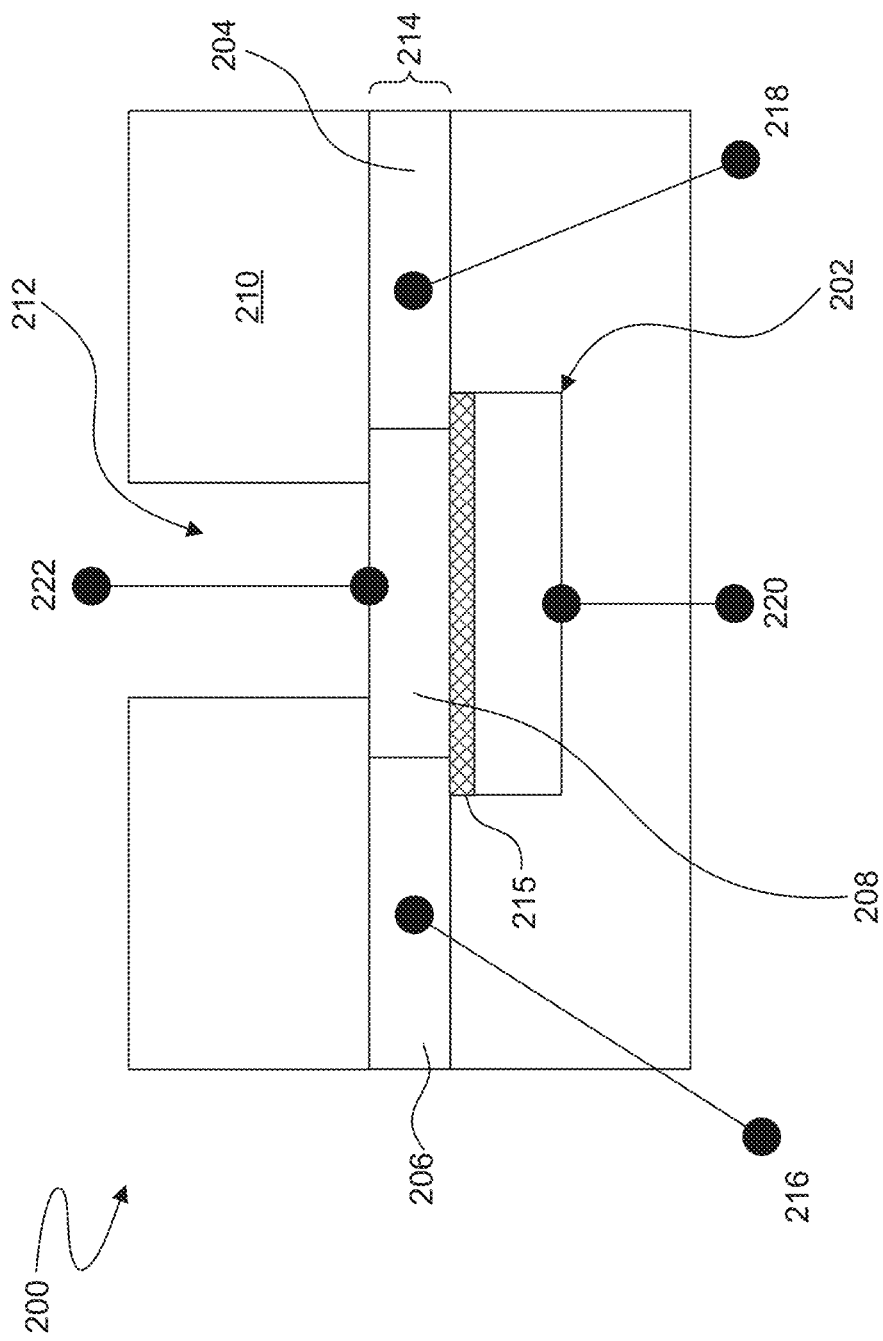
FIG. 2 illustrates a cross-sectional view of an exemplary dual-gate back-side sensing FET sensor, according to some embodiments.

FIG. 2 illustrates an exemplary dual gate back-side sensing FET sensor 200, according to some embodiments. Dual gate back-side sensing FET sensor 200 includes a control gate 202 formed over substrate 214 and separated therefrom by an intervening dielectric 215 disposed on substrate 214. Substrate 214 further includes a source region 204, a drain region 206, and a channel region 208 between source region 204 and drain region 206. In some embodiments, substrate 214 has a thickness between about 100 nm and about 130 nm. Gate 202, source region 204, drain region 206, and channel region 208 may be formed using suitable CMOS process technology. Gate 202, source region 204, drain region 206, and channel region 208 form a FET. An isolation layer 210 is disposed on the opposing side of substrate 214 from gate 202. In some embodiments, isolation layer 210 has a thickness of about 1 µm. In this disclosure the side of substrate 214 over which gate 202 is disposed is referred to as the "front-side" of substrate 214. Similarly, the side of substrate 214 on which isolation layer 210 is disposed is referred to as the "back-side."

An opening 212 is provided in isolation layer 210. Opening 212 may be substantially aligned with gate 202. In other embodiments, opening 212 is larger than gate 202 and may extend over multiple dual gate back-side sensing FET sensors. An interface layer (not shown) may be disposed in opening 212 on the surface of channel region 208. The interface layer may be operable to provide an interface for positioning and immobilizing one or more receptors for detection of biomolecules or bio-entities. Further details regarding the interface layer are provided herein.

Dual gate back-side sensing FET sensor 200 includes electrical contacts 216 and 218 to drain region 206 and source region 204, respectively. A front-side gate contact 220 may be made to gate 202, while a back-side gate contact 222 may be made to active region 208. It should be noted that back-side gate contact 222 does not need to physically contact substrate 214 or any interface layer over substrate 214. Thus, while a FET can use a gate contact to control conductance of the semiconductor between the source and drain (e.g., the channel), dual gate back-side sensing FET sensor 200 allows receptors formed on a side opposing gate 202 of the FET device to control the conductance, while gate 202 provides another region to control the conductance. Therefore, dual gate back-side sensing FET sensor 200 may be used to detect one or more specific biomolecules or bio-entities in the environment around and/or in opening 212, as discussed in more detail using various examples herein.

Dual gate back-side sensing FET sensor 200 may be connected to: additional passive components such as resistors, capacitors, inductors, and/or fuses; other active components, including p-channel field effect transistors (PFETs), n-channel field effect transistors (NFETs), metal-oxide-semiconductor field effect transistors (MOSFETs), high voltage transistors, and/or high frequency transistors; other suitable components; and/or combinations thereof. It is further understood that additional features can be added in dual gate back-side sensing FET sensor 200, and some of the features described can be replaced or eliminated, for additional embodiments of dual gate back-side sensing FET sensor 200.

Figure 3A:
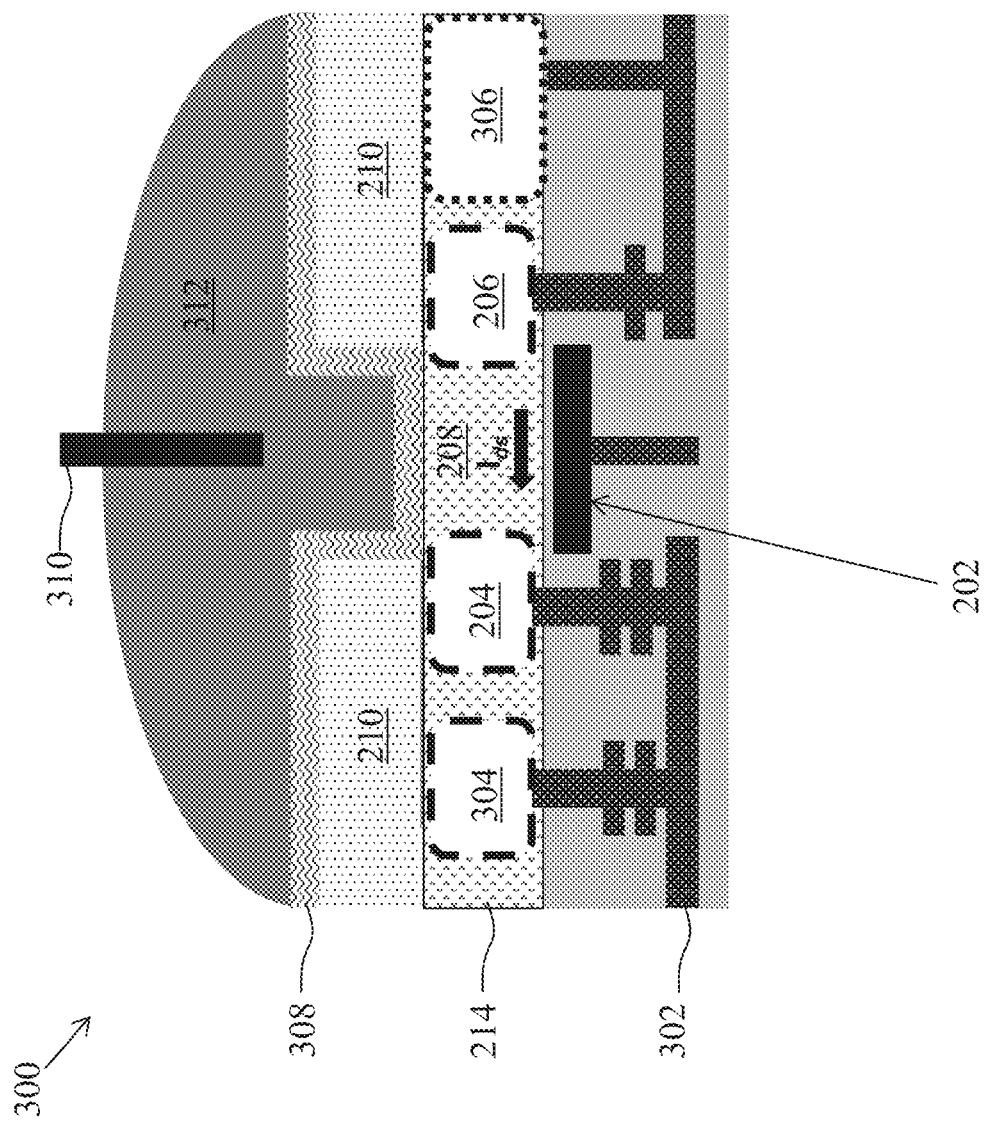
FIG. 3A illustrates a cross-sectional view of an exemplary dual gate back-side sensing FET sensor, according to some embodiments.

Referring to FIG. 3A, a cross section of an example dual gate back-side sensing FET sensor 300 is provided, according to some embodiments. The dual gate back-side sensing FET sensor 300 is one implementation of dual gate back-side sensing FET sensor 200. Thus previously described elements from FIG. 2 are labeled with element numbers from FIG. 2 and their descriptions are not repeated here. Dual gate back-side sensing FET sensor 300 includes gate 202, source region 204, drain region 206, and channel region 208, where source region 204 and drain region 206 are formed within substrate 214. Gate 202, source region 204, drain region 206, and channel region 208 form a FET. It should be noted that the various components of FIG. 3A are not intended to be drawn to scale and are exaggerated for visual convenience, as would be understood by a person skilled in the relevant art.

In some embodiments, dual gate back-side sensing FET sensor 300 is coupled to various layers of metal interconnects 302 that make electrical connection with the various doped regions and other devices formed within substrate 214. Metal interconnects 302 may be manufactured using fabrication processes well known to a person skilled in the relevant art.

Dual gate back-side FET sensor 300 may include a body region 304 separate from source region 204 and drain region 206. Body region 304 may be used to bias the carrier concentration in active region 208 between source region 204 and drain region 206. In some embodiments, a negative voltage bias may be applied to body region 304 to improve the sensitivity of dual gate back-side FET sensor 300. In some embodiments, body region 304 is electrically connected to source region 204. In some embodiments, body region 304 is electrically grounded.

Dual gate back-side FET sensor 300 may be coupled to additional circuitry 306 fabricated within substrate 214. Circuitry 306 may include any number of MOSFET devices, resistors, capacitors, and/or inductors to form circuitry to aid in the operation of dual gate back-side sensing FET sensor 300. Circuitry 306 may represent a readout circuit used to measure a signal from dual gate back-side FET sensor 300 that is indicative of analyte detection. Circuitry 306 may include amplifiers, analog to digital converters (ADCs), digital to analog converters (DACs), voltage generators, logic circuitry, and/or DRAM memory, to name a few examples. In some embodiments, circuitry 306 includes digital components and does not measure an analog signal from dual gate back-side FET sensor 300. All or some of the components of additional circuitry 306 may be integrated in the same substrate 214 as dual gate back-side FET sensor 300. It should be understood that many FET sensors, each substantially similar to dual gate back-side FET sensor 300, may be integrated in substrate 214 and coupled to additional circuitry 306. In another example, all or some of the components of additional circuitry 306 are provided on another semiconductor substrate separate from substrate 214. In yet another example, some components of additional circuitry 306 are integrated in the same substrate 214 as dual gate back-side FET sensor 300, and some components of additional circuitry 306 are provided on another semiconductor substrate separate from substrate 214.

Still referring to the illustrative example of FIG. 3A, dual gate back-side sensing FET sensor 300 includes an interface layer 308 deposited over isolation layer 210 and within the opening over channel region 208. In some embodiments, interface layer 308 has a thickness between about 20 Å and about 40 Å. Interface layer 308 may be a high-K dielectric material, such as hafnium silicate, hafnium oxide, zirconium oxide, aluminum oxide, tantalum pentoxide, hafnium dioxide-alumina ($HfO_2$—$Al_2O_3$) alloy, or any combinations thereof. Interface layer 308 may act as a support for the attachment of capture reagents as will be discussed in more detail later in the section directed to biological sensing. A solution 312 is provided over the reaction site of dual gate back-side sensing FET sensor 300, and a fluid gate 310 is placed within solution 312. Solution 312 may be a buffer solution containing capture reagents, target reagents, wash solution, or any other biological or chemical species.

An example operation of dual gate back-side FET sensor 300 as a pH sensor will now be described. Briefly, fluid gate 310 is used to provide an electrical contact to the "second gate" of the dual gate back-side sensing FET sensor. Solution 312 is provided over the reaction site of dual gate back-side sensing FET sensor 300, and fluid gate 310 is placed within solution 312. The pH of the solution is generally related to the concentration of hydrogen ions [$H^+$] in the solution. The accumulation of the ions near the surface of interface layer 308 above channel region 208 affects the formation of the inversion layer within channel region 208 that forms the conductive pathway between source region 204 and drain region 206. In some embodiments, a current $I_{ds}$ flows from drain region 206 to source region 204.

The current $I_{ds}$ may be measured to determine the pH of solution 312. In some embodiments, fluid gate 310 is used as the gate of the transistor during sensing while gate 202 remains floating. In some embodiments, fluid gate 310 is used as the gate of the transistor during sensing while gate 202 is biased at a given potential. For example, gate 202 may be biased at a potential between −2V and 2V depending on the application, while fluid gate 310 is swept between a range of voltages. In some embodiments, fluid gate 310 is biased at a given potential (or grounded) while gate 202 is used as the gate of the transistor (e.g., its voltage is swept across a range of potentials) during sensing. Fluid gate 310 may be formed from platinum or may be formed from any other commonly used material(s) for reference electrodes in electrochemical analysis. An example of a reference electrode is an Ag/AgCl electrode, which has a stable potential value of about 0.230 V.

Figure 3C:
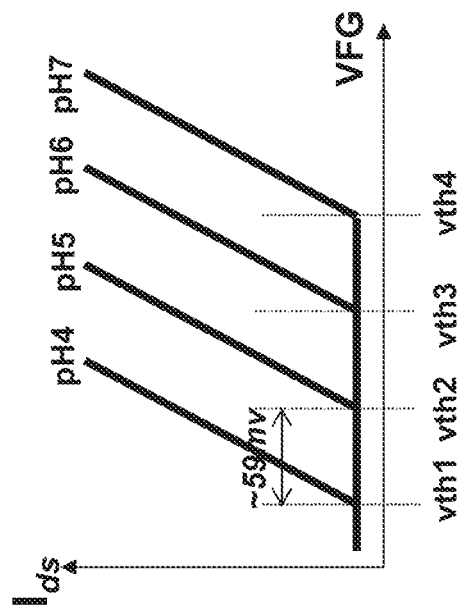
FIGS. 3B and 3C illustrate using the dual gate back-side sensing FET sensor as a pH sensor, according to some embodiments.
Figure 3B:
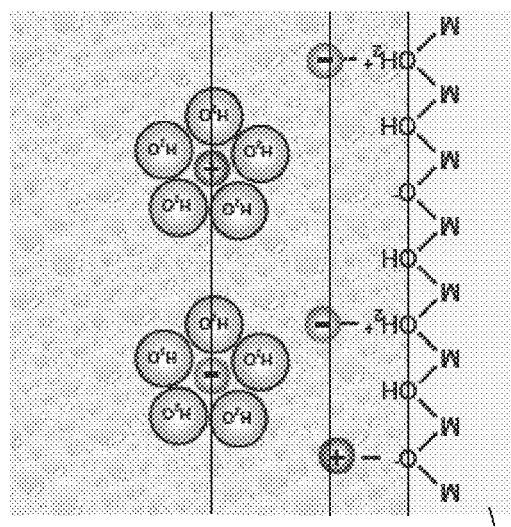

FIG. 3B shows ions in solution binding to a surface of interface layer 308. A top-most atomic layer of interface layer 308 is depicted as the various dangling [$O^-$], [OH], and [$OH_2^+$] bonds. As the ions accumulate on the surface, the total surface charge affects the threshold voltage of the transistor. As used herein, the threshold voltage is the minimum potential between the gate and the source of a FET sensor that is required to form a conductive path of minority carriers between the source and the drain of the FET sensor. The total charge also directly relates to a pH of the solution, as a higher accumulation of positive charge signifies a lower pH while a higher accumulation of negative charge signifies a higher pH.

FIG. 3C illustrates an example change in threshold voltage that results due to different pH values in an n-channel FET sensor. As can be observed in this example, a 59 mV increase in threshold voltage roughly signifies an increase of one in the pH of the solution. In other words, one pH change results in total surface charge equivalent of 59 mV when measured as the voltage required to turn on the transistor.

Changing the threshold voltage of dual gate back-side FET sensor 300 also changes a time it takes to form a conductive path between source region 204 and drain region 206 for a given voltage input to either fluid gate 310 or gate 202. This time delay in "turning on" the FET sensor may be quantified using digital circuitry and used to determine an analyte concentration, according to some embodiments.

Readout Circuits

FIGS. 4A-4C illustrate example logic gates that utilize a bioFET sensor as at least one of the transistors in the logic circuit, according to some embodiments. FIG. 4A illustrates an inverter 401 that includes two transistors: a p-channel transistor 402 and a bioFET sensor 404. BioFET sensor 404 may be a dual-gate back-side FET sensor as described with reference to FIGS. 3A-C. In the arrangement of inverter 401, a source terminal of p-channel transistor 402 is connected to a positive rail voltage (VDD) while a drain terminal of p-channel transistor 402 is connected to a drain terminal of bioFET sensor 404. A source terminal of bioFET sensor 404 is connected to ground. The gates of both p-channel transistor 402 and bioFET sensor 404 are tied together and receive an input signal 406. An output signal 408 is generated at the drain terminals of p-channel transistor 402 and bioFET sensor 404. In an example where bioFET sensor 404 is a dual-gate back-side FET sensor, the gate of bioFET sensor 404 that receives input signal 406 is a front gate (similar to gate 202 in FIG. 3A), while a fluid gate is biased at a given potential between about 0 mV and about 500 mV.

P-channel transistor 402 may not include any biological interface and may not be exposed to any solution during operation. BioFET sensor 404 may have a surface (such as, for example, interface layer 308 for a dual-gate FET design) that is exposed to a solution carrying an analyte to be detected. The analyte may bind to capture molecules designed to bind to only that specific analyte. The capture molecules may already be bound to the surface of bioFET sensor 404 before the solution carrying the analyte is introduced. In some embodiments, bioFET sensor 404 represents one sensor output of an array of sensors that may total over 100, over 1,000, or over 10,000 bioFET sensors. In some embodiments, bioFET sensor 404 represents multiple bioFET sensors arranged in an array format and that are electrically coupled at their common terminals.

Input signal 406 is inverted by inverter 401 to produce output signal 408. That is, a rising edge transition of input signal 406 results in a falling edge transition of output signal 408, while a falling edge transition of input signal 406 results in a rising edge transition of output signal 408. During a rising edge transition of input signal 406, a positive voltage is applied to the gate of bioFET sensor 404, thus turning it on (assuming bioFET sensor 404 is an n-channel device). The time it takes for bioFET sensor 404 to turn on is related to its threshold voltage. Binding of various charged analytes to the surface of bioFET sensor 404 can change its threshold voltage, according to some embodiments. This delay in turning on bioFET sensor 404 may be quantified in output signal 408 as $\Delta t$, where $\Delta t$ is the time delay in turning on bioFET sensor 404 due to a change in the number of charged particles on or near the surface of bioFET sensor 404. The addition or subtraction of charge may be caused by a change in pH in the solution over bioFET sensor 404 or by binding charged analytes to a surface of bioFET sensor 404. The time delay $\Delta t$ in output signal 408 may be a positive delay or a negative delay depending on the charge polarity that is present at or near the surface of bioFET sensor 404, according to some embodiments.

FIG. 4B illustrates another example of an inverter 403 that includes a bioFET sensor 410 and an n-channel transistor 412. BioFET sensor 410 may be similar to bioFET sensor 404, except that bioFET sensor 410 is a p-channel device while bioFET sensor 404 is an n-channel device. In the arrangement of inverter 403, a source terminal of bioFET sensor 410 is connected to a positive rail voltage (VDD) while a drain terminal of bioFET sensor 410 is connected to a drain terminal of n-channel transistor 412. A source terminal of n-channel transistor 412 is connected to ground. The gates of both bioFET sensor 410 and n-channel transistor 412 are tied together and receive an input signal 414.

An output signal 416 is generated at the drain terminals of bioFET sensor 410 and n-channel transistor 412.

Input signal 414 is inverted by inverter 403 to produce output signal 416. Because bioFET sensor 410 is a p-channel device in inverter 403, a falling edge transition of input signal 414 results in a delayed rising edge transition of output signal 416. The time delay Δt is proportional to the change in threshold voltage of bioFET sensor 410. The time delay Δt in output signal 416 may be a positive delay or a negative delay depending on the charge polarity that is present at or near the surface of bioFET sensor 410, according to some embodiments.

FIG. 4C illustrates another example of an inverter 403 that includes bioFET sensor 410 acting as the p-channel device and bioFET sensor 404 acting as the n-channel device. The gates of both bioFET sensor 404 and bioFET sensor 410 are tied together and receive input signal 406/414. Output signal 408/416 is generated at the drain terminals of bioFET sensor 404 and bioFET sensor 410. Both rising and falling edge transitions of input signal 406/414 are inverted and delayed at output signal 408/416 with the time delay being related to the change in the threshold voltages of bioFET sensor 404 and bioFET sensor 410, respectively.

Both bioFET sensor 404 and bioFET sensor 410 may be functionalized with the same capture probes to detect the same analyte. In some embodiments, bioFET sensor 404 is functionalized with a different capture probe than bioFET sensor 410, such that binding of a particular target analyte causes a time delay during rising edge transitions or during falling edge transitions, according to some embodiments.

By incorporating bioFET sensors as specific transistors of a logic gate, the threshold voltage changes of the bioFET sensor can be calculated based on the time delay in the output signal. It should be noted that other logic gates beyond inverters can also be used to produce outputs having a time delay proportional to the sensing output of the bioFET sensors. Accordingly, bioFET sensors may be incorporated in AND gates, NAND gates, OR gates, NOR gates, or XOR gates.

Figure 5:
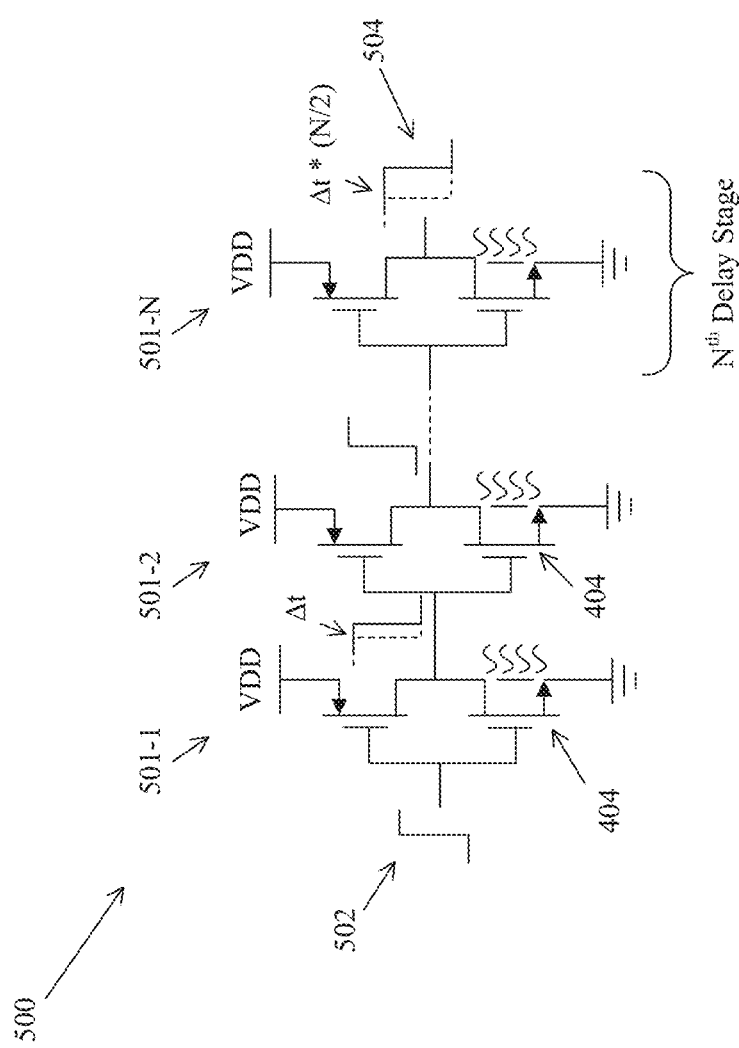
FIG. 5 illustrates multiple logic gates using bioFET sensors coupled in cascade, according to some embodiments.

FIG. 5 illustrates a delay chain 500 that includes N logic gate stages identified as 501-1 through 501-N coupled together in cascade, according to some embodiments. In one embodiment, each logic gate stage includes at least two FET devices, where at least one of the FET devices is a bioFET sensor, such as bioFET sensor 404 illustrated in each of logic gate stage 501-1 and logic gate stage 501-2. In another embodiment, each logic gate stage includes one bioFET sensor and at least one resistive element using known resistor-transistor logic (RTL) configurations. Delay chain 500 has an input signal 502 at a first logic gate 501-1 and generates an output signal 504 at the Nth logic gate (logic gate 501-N). The output of each logic gate stage is received as an input to a subsequent logic gate stage in the chain, except for the Nth logic gate stage. As noted above, logic gate stages 501-1 through 501-N are illustrated as inverters, but any logic gates could be coupled together in cascade to form delay chain 500 as would be understood by a person skilled in the relevant art.

By coupling multiple logic gates together, the time delay generated from each bioFET sensor is added together. If Δt is the time delay generated from a single inverter stage where the bioFET sensor is activated, then the final time delay in output signal 504 of the Nth stage is roughly equal to Δt*(N/2). The total number of stages N is divided by 2 because half of the stages activate the bioFET sensor in the example illustrated in FIG. 5. In an example where both the n-channel and p-channel transistors of each inverter stage are bioFET sensors, the output signal of the Nth stage would be roughly equal to Δt*N.

In some embodiments, an output signal may be measured between any two stages in delay chain 500 to probe any bioFET sensors from the preceding stages in the chain. For example, if an output signal is measured between the 8$^{th}$ and 9$^{th}$ stages of delay chain 500, then the time delay of that output signal would be proportional to the sensing activity of the bioFET sensors from stages 1-8, but not from stages 9-N. In this way, multiple bioFET sensors may be probed within the same delay chain 500.

Figure 6:
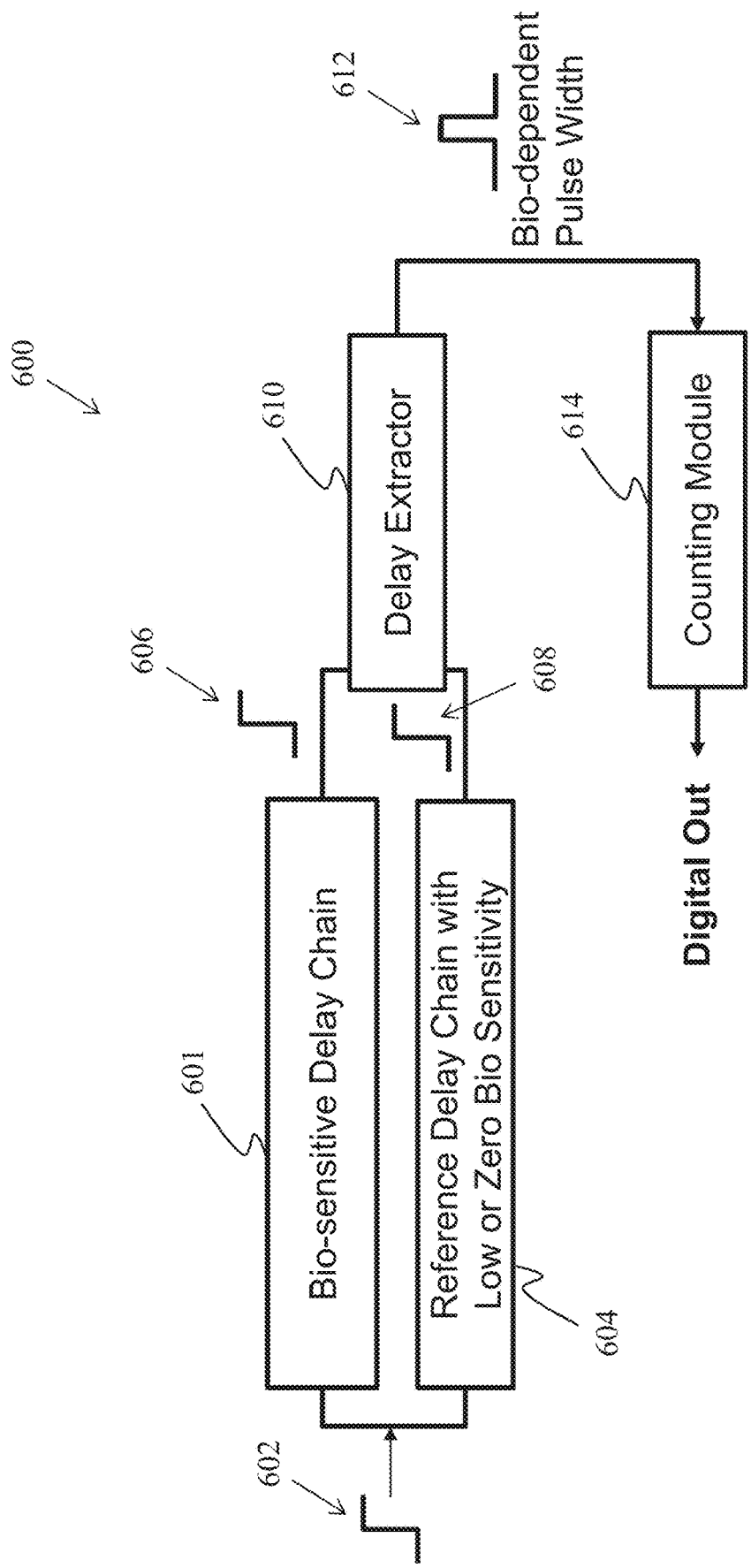
FIG. 6 illustrates a readout circuit for performing sensing using bioFET sensors, according to some embodiments.

FIG. 6 illustrates an example readout circuit 600 designed to quantify the time delay produced as a result of the operation of one or more bioFET sensors, according to some embodiments. Readout circuit 600 includes a bio-sensitive delay chain 601 and a reference delay chain 604 that each receives a same input signal 602, according to some embodiments. Bio-sensitive delay chain 601 includes a series of cascaded logic circuits that includes at least one bioFET sensor. One example of bio-sensitive delay chain 601 is delay chain 500. Bio-sensitive delay chain 601 may include any type of logic gate coupled together in cascade, where each stage of the chain includes at least one bioFET sensor. Bio-sensitive delay chain 601 generates a sensor output signal 606 that may have a bio-sensitive delay in the time domain.

Reference delay chain 604 may include a series of logic gates coupled in cascade to provide a reference output signal 608. According to some embodiments, the transistors that make up the logic gates of reference delay chain 604 do not have biosensing properties. In some embodiments, one or more of the transistors that make up the logic gates of reference delay chain 604 are functionalized with different capture reagents than those that are on the bioFET sensors in bio-sensitive delay chain 601. The transistors of reference delay chain 604 may be physically located in the vicinity of the bioFET sensors from bio-sensitive delay chain 601 such that a solution containing a target analyte is disposed over a surface of both the bioFET sensors from bio-sensitive delay chain 601 and the transistors of reference delay chain 604. In another example, the transistors of reference delay chain 604 are physically located away from the bioFET sensors from bio-sensitive delay chain 601 such that the transistors of reference delay chain 604 are not in contact with any solution.

According to some embodiments, reference delay chain 604 includes the same number and type of logic gate stages as bio-sensitive delay chain 601. In one example, reference delay chain 604 is designed such that a time delay between input signal 602 and reference output signal 608 is substantially equal to a time delay between input signal 602 and sensor output signal 606 when no target analytes are bound to the bioFET sensors in bio-sensitive delay chain 601. Since both bio-sensitive delay chain 601 and reference delay chain 604 receive the same input signal 602, a difference in the time domain between reference output signal 608 and sensor output signal 606 is associated with the amount of target analyte detected by the bioFET sensors in bio-sensitive delay chain 601.

According to some embodiments, reference delay chain 604 is removed and input signal 602 is also used as reference output signal 608. In this arrangement, a time delay between reference output signal 608 and sensor output signal 606 in a control experiment is compared to a time delay between reference output signal 608 and sensor output signal 606 after exposing the bioFET sensors to a solution with the target analyte to determine a concentration and/or presence of the target analyte.

A delay extractor 610 is used to determine the time domain difference between sensor output signal 606 and reference output signal 608, according to some embodiments. Delay extractor generates a pulse-width signal 612 having a width that is dependent on the output of the bioFET sensors. Delay extractor 610 may include an XOR gate designed to receive output signal 606 and reference output signal 608 as inputs and generate pulse-width signal 612 as an output. In one example, pulse-width signal 612 has a width in the nanosecond range (e.g., between 1 ns and 1000 ns.)

According to some embodiments, readout circuit 600 includes a counting module 614 that receives pulse-width signal 612 and outputs a digital count corresponding to a width of pulse-width signal 612. Counting module 614 may include any digital counter circuitry as would be understood by a person having ordinary skill in the art.

Figure 7:
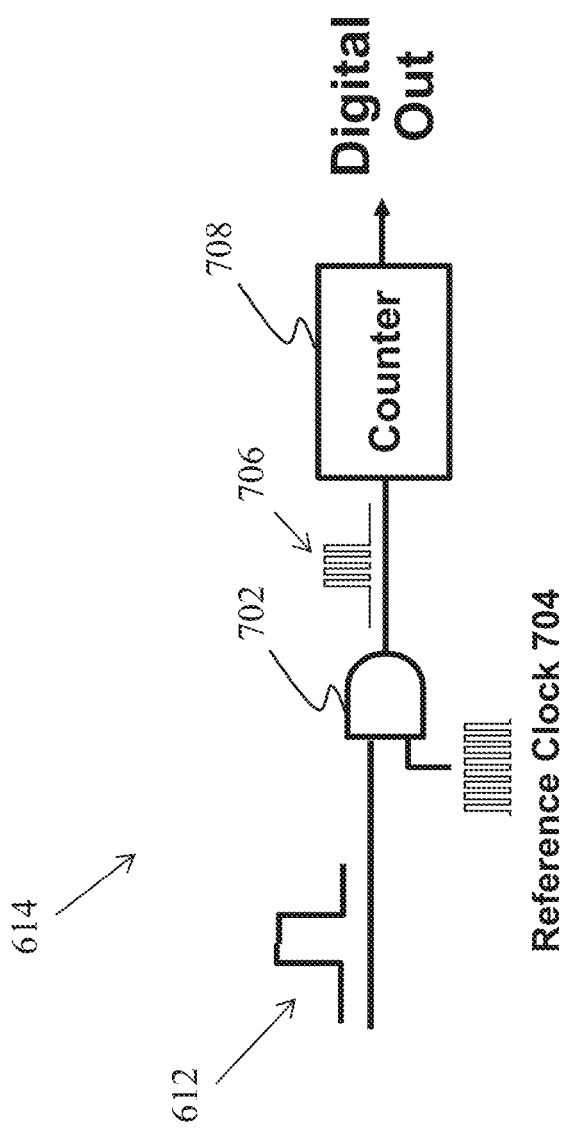
FIG. 7 illustrates components of a counting module, according to some embodiments.

FIG. 7 illustrates a representation of counting module 614, according to some embodiments. Counting module 614 includes an AND gate 702 designed to receive pulse-width signal 612 and a reference clock signal 704. AND gate 702 generates a pulse count signal 706. Pulse count signal 706 includes a given number of clock cycles within a width of pulse-width signal 612. Reference clock 704 may have a frequency between about 800 MHz and 1.2 GHz.

Pulse count signal 706 is received by a counter 708, according to some embodiments. Counter 708 may include flip flops or latches designed to count a number of clock cycles present in pulse count signal 706. In one example, counter 708 includes a series of JK flip flops coupled together with the output of a given JK flip flop coupled to the clock input of the next JK flip flop in the series. A binary digital count may be an output from counter 708.

Figure 8:
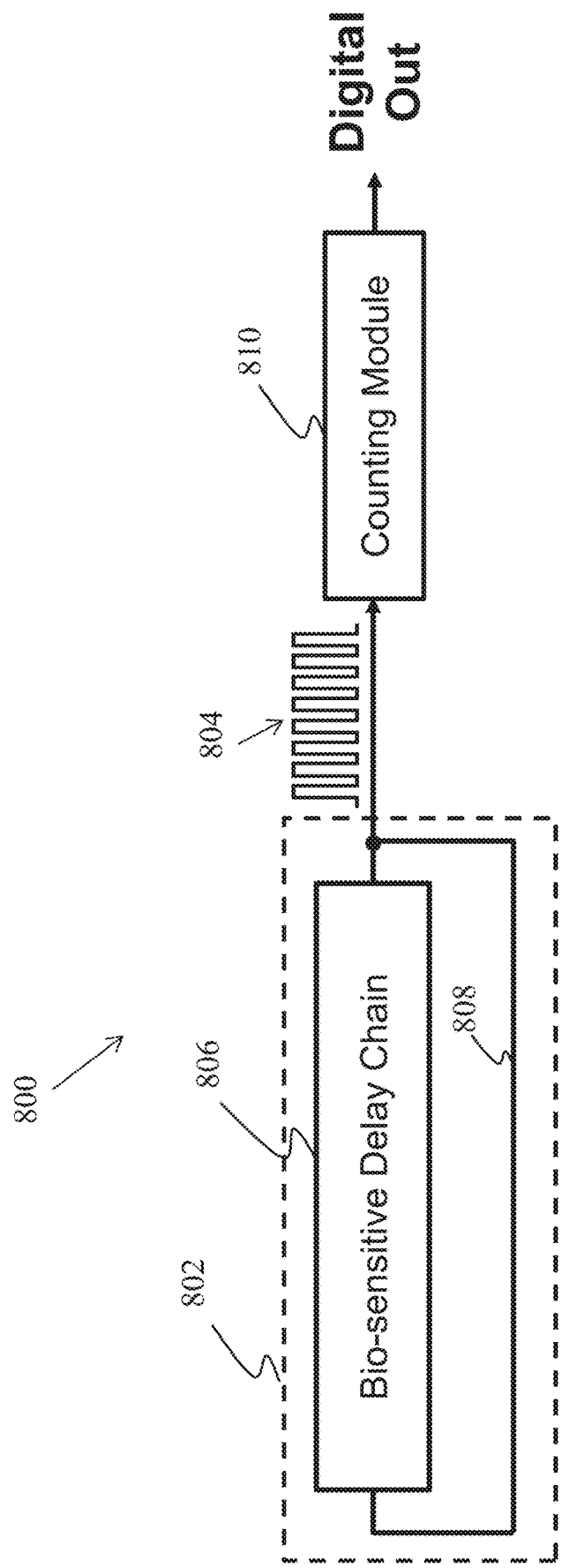
FIG. 8 illustrates another readout circuit for performing sensing using bioFET sensors, according to some embodiments.

FIG. 8 illustrates another example readout circuit 800 designed to probe the operation of one or more bioFET sensors, according to some embodiments. Readout circuit 800 includes a bio-sensitive oscillator 802 to produce an oscillating sensor output 804. Oscillator 802 may include a bio-sensitive delay chain 806, which may be similar to delay chain 500. As such, bio-sensitive delay chain 806 may include a series of inverters coupled in cascade that includes at least one bioFET sensor or a series of any cascaded logic circuits that includes at least one bioFET sensor.

To form the oscillating sensing output, the output of bio-sensitive delay chain 806 is fed back through feedback line 808 to be received as an input to bio-sensitive delay chain 806. This creates a ring oscillator with a constantly oscillating sensor output 804 having a frequency based on the number of stages in bio-sensitive delay chain 806, the size of the transistors used in the various stages, and the operation of the bioFET sensors in bio-sensitive delay chain 806. For example, a target analyte bound to a surface of the bioFET sensors may increase the threshold voltage of the bioFETs, thus decreasing a resulting frequency of oscillating sensor output 804.

According to some embodiments, readout circuit 800 includes a counting module 810 that receives oscillating sensor output 804 and outputs a digital count corresponding to a frequency of oscillating sensor output 804. Counting module 810 may include any type of digital counter circuitry as would be understood by a person having ordinary skill in the art.

Figure 9:
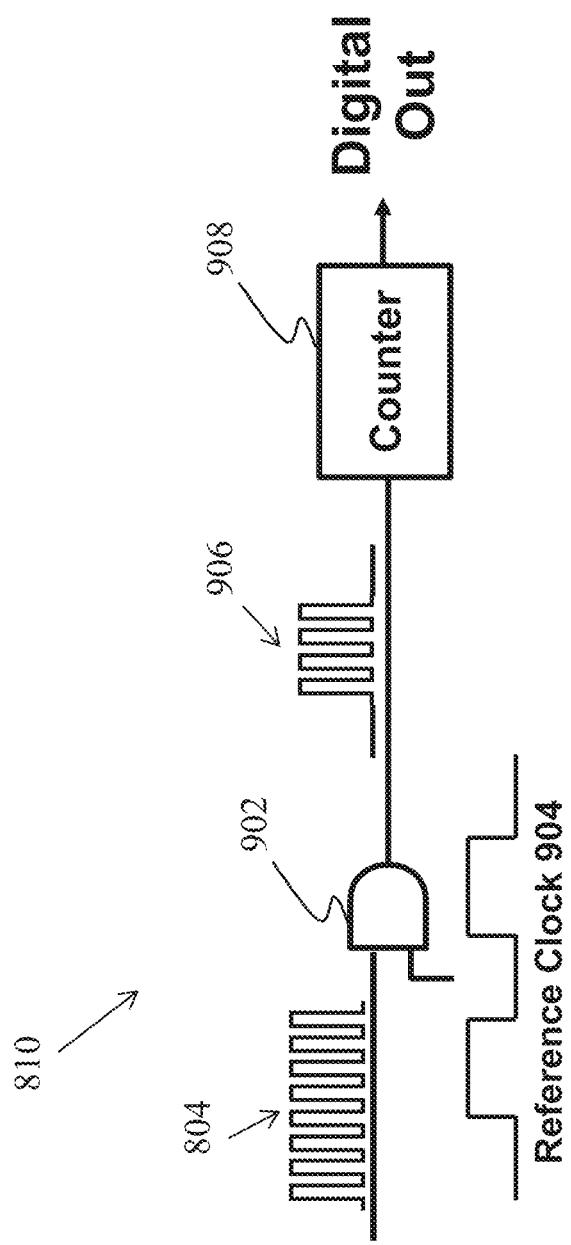
FIG. 9 illustrates components of a counting module, according to some embodiments.

FIG. 9 illustrates a representation of counting module 810, according to some embodiments. Counting module 810 includes an AND gate 902 designed to receive oscillating sensor output 804 and a reference clock signal 904. AND gate 902 generates a count signal 906. Count signal 906 includes a number of cycles of oscillating sensor output 804 within one clock cycle of reference clock 904. The number of cycles of oscillating sensor output 804 may be counted to provide an indication of the width of each cycle (correlated with the frequency of oscillating sensor output 904.) Reference clock 904 may have a frequency between about 50 KHz and 150 KHz. In one example, a frequency of reference clock 904 is chosen to be at least 100 times lower, at least 1000 times lower, or at least 10,000 times lower than a frequency of oscillating sensor output 804.

Count signal 906 is received by a counter 908, according to some embodiments. Counter 908 may include flip flops or latches designed to count a number of clock cycles present in count signal 906. In one example, counter 908 includes JK flip flops coupled together in cascade with the output of a given JK flip flop coupled to the clock input of the next JK flip flop. A binary digital count may be output from counter 908.

Figure 10:
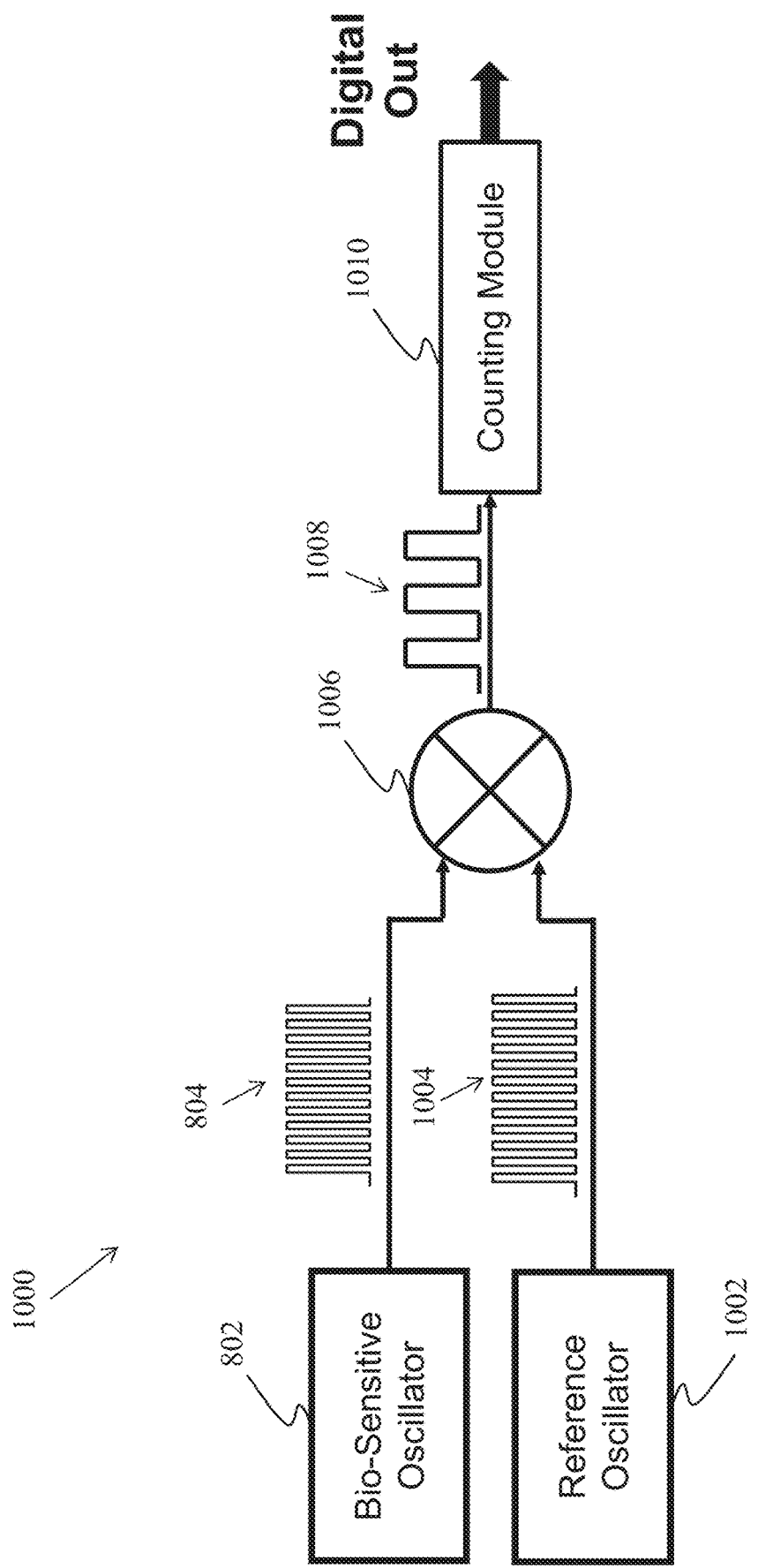
FIG. 10 illustrates another readout circuit for performing sensing using bioFET sensors, according to some embodiments.

FIG. 10 illustrates another example readout circuit 1000 designed to probe the operation of one or more bioFET sensors, according to some embodiments. Readout circuit 1000 includes bio-sensitive oscillator 802 to produce an oscillating sensor output 804, as described with reference to FIG. 8. Readout circuit also includes a reference oscillator 1002 designed to generate reference oscillating signal 1004. According to some embodiments, reference oscillating signal 1004 has a frequency substantially equal to a frequency of oscillating sensor output 804 when no target analyte is bound to any of the bioFET sensors. In this way, any frequency change to oscillating sensor output 804 due to the presence of a target analyte will provide a difference between oscillating sensor output 804 and reference oscillating signal 1004. Reference oscillating signal 1004 may have a frequency between about 150 MHz and about 250 MHz.

According to some embodiments, the transistors that make up the logic gates of reference oscillator 1002 do not have biosensing properties. In some embodiments, one or more of the transistors that make up the logic gates of reference oscillator 1002 are functionalized with different capture reagents than those that are on the bioFET sensors in bio-sensitive oscillator 802. The transistors of reference oscillator 1002 may be physically located in the vicinity of the bioFET sensors from bio-sensitive oscillator 802 such that a solution containing a target analyte is disposed over a surface of both the bioFET sensors from bio-sensitive oscillator 802 and the transistors of reference oscillator 1002. In another example, the transistors of reference oscillator 1002 are physically located away from the bioFET sensors from bio-sensitive oscillator 802 such that the transistors of reference oscillator 1002 are not in contact with any solution.

Readout circuit 1000 also includes a mixer 1006 that receives oscillating sensor output 804 and reference oscillating signal 1004 as inputs. Mixer 1006 may be a down-conversion mixer that generates a down-converted signal 1008. In some embodiments, mixer 1006 includes at least one D flip-flop where reference oscillating signal 1004 is received as a clock input of the D flip-flop and oscillating sensor output 804 is received at the data input of the D flip-flop. Down converted signal 1008 corresponds to a difference in the oscillation frequency between oscillating sensor output 804 and reference oscillating signal 1004. When no detection occurs at the bioFET sensors, down converted signal 1008 has substantially no oscillating signal. However, when target analyte binds at the bioFET sensors, down converted signal 1008 will have an oscillation frequency substantially equal to the difference in the oscillation frequency between oscillating sensor output 804 and reference oscillating signal 1004 and that corresponds to the amount of target analyte present. When the bioFET sensors are used as pH sensors, a change of 1 pH may be roughly equivalent to a 2 MHz shift in the frequency of oscillating sensor output 804, according to some embodiments.

According to some embodiments, readout circuit 1000 includes a counting module 1010 that receives down-converted signal 1008 and outputs a digital count corresponding to a frequency of down-converted signal 1008. Counting module 1010 may include any type of digital counter circuitry as would be understood by a person having ordinary skill in the art.

Figure 11:
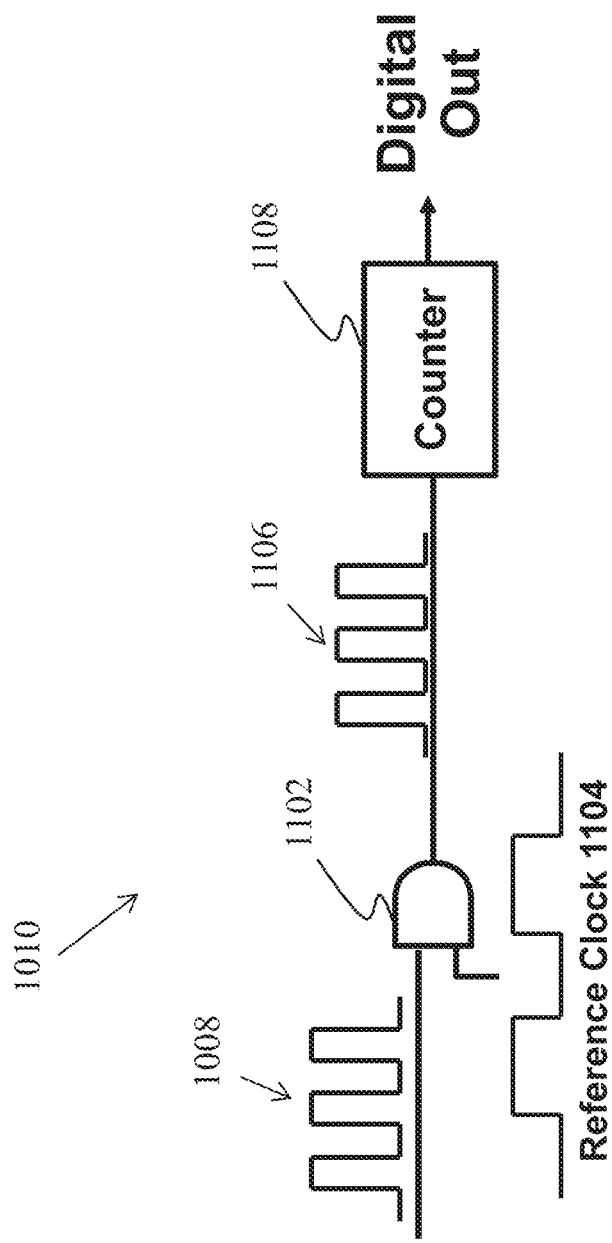
FIG. 11 illustrates components of a counting module, according to some embodiments.

FIG. 11 illustrates a representation of counting module 1010, according to some embodiments. Counting module 1010 includes an AND gate 1102 designed to receive down-converted signal 1008 and a reference clock signal 1104. AND gate 1102 generates a count signal 1106. Count signal 1106 includes a number of cycles of down-converted signal 1008 within one clock cycle of reference clock 1104. The number of cycles of down-converted signal 1008 may be counted to provide an indication of the width of each cycle (correlated with the frequency of down-converted signal 1008.) Reference clock 1104 may have a frequency between about 5 KHz and about 50 KHz. In one example, a frequency of reference clock 1104 is chosen to be at least 100 times lower, at least 1,000 times lower, or at least 10,000 times lower than a frequency of down-converted signal 1008.

Count signal 1106 is received by a counter 1108, according to some embodiments. Counter 1108 may include flip flops or latches designed to count a number of clock cycles present in count signal 1106. In one example, counter 1108 includes a series of JK flip flops coupled together with the output of a given JK flip flop coupled to the clock input of the next JK flip flop in the series. A binary digital count may be output from counter 1108.

Figure 12:
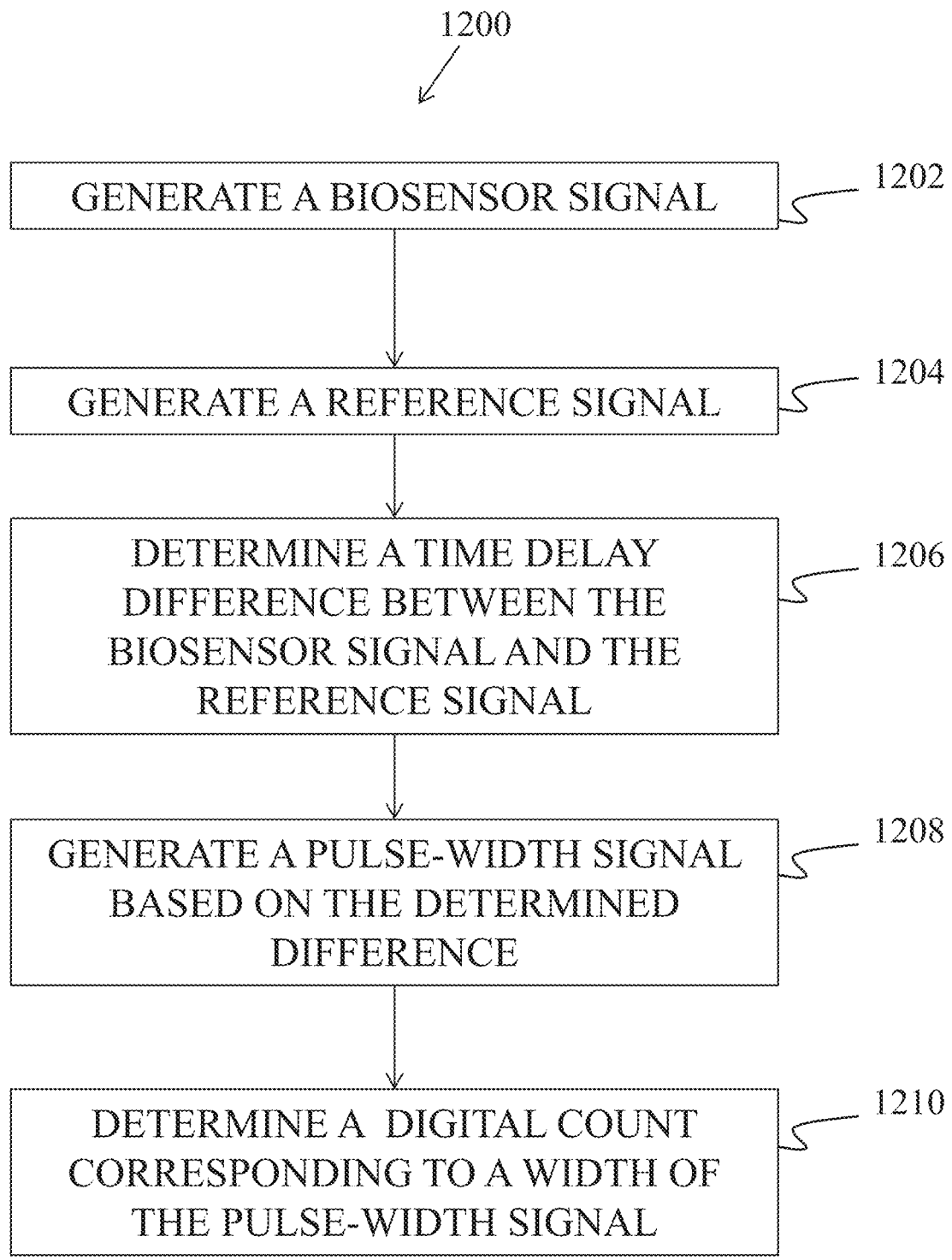
FIG. 12 illustrates a flow diagram of an exemplary method of measuring a sensing signal from one or more bioFET sensors, according to some embodiments.

Referring to FIG. 12, an example method 1200 is presented. Method 1200 may be performed by readout circuit 600 to measure the sensor output of one or more bioFET sensors in a sensor array. Other operations relating to signal filtering or any other signal processing not illustrated in method 1200 may be performed either before, between, or after the illustrated operations of method 1200. The various operations of method 1200 may be performed in a different order than the one illustrated.

At block 1202, a biosensor signal is generated. The biosensor signal may be an output of a cascaded series of logic gates, where each logic gate includes at least one bioFET sensor. In one example, each of the cascaded logic gates are inverter circuits, and a time delay between an input signal to the cascaded series of logic gates and the biosensor signal at the output corresponds to detection of a target analyte.

At block 1204, a reference signal is generated. The reference signal may be generated from another cascaded series of logic gates that is arranged similarly to those that generate the biosensor signal. In some embodiments, these cascaded series of logic gates do not include bioFET sensors.

At block 1206, a time delay difference is determined between the biosensor signal and the reference signal. The determined time delay difference may correspond to a concentration of target analyte that is bound to the bioFET sensors. The biosensor signal may be delayed in the time domain compared to the reference signal due to changes in the threshold voltages of the bioFET sensors.

At block 1208, a pulse-width signal is generated based on the determined time difference. The pulse-width signal may be generated using an XOR gate that receives the biosensor signal and the reference signal as inputs. A width of the pulse corresponds to a time difference between the biosensor signal and the reference signal.

At block 1210, a digital count corresponding to a width of the pulse width signal is determined. A counting module may be used to determine the digital count that includes a counter and also uses a reference clock to provide a number of clock cycles for a given pulse width. The reference clock may have a frequency between about 800 MHz and 1.2 GHz. The counter may use cascaded JK flip flops coupled together with the output of a given JK flip flop coupled to the clock input of the next JK flip flop.

Figure 13:
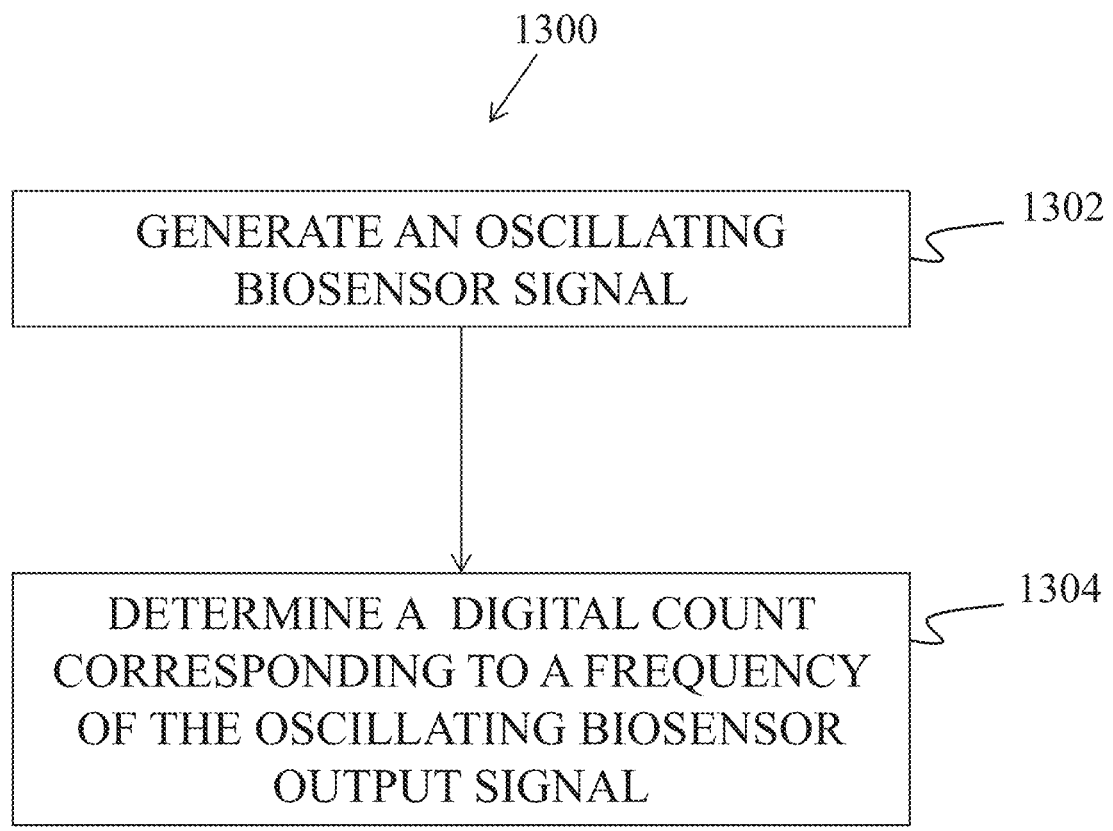
FIG. 13 illustrates a flow diagram of another exemplary method of measuring a sensing signal from one or more bioFET sensors, according to some embodiments.

Referring to FIG. 13, an example method 1300 is presented. Method 1300 may be performed by readout circuit 800 to measure the sensor output of one or more bioFET sensors in a sensor array. Other operations relating to signal filtering or any other signal processing not illustrated in method 1300 may be performed either before, between, or after the illustrated operations of method 1300. The various operations of method 1300 may be performed in a different order than the one illustrated.

At block 1302, an oscillating biosensor signal is generated. The oscillating biosensor signal may be an output of a cascaded series of inverters, where the output is also fed back to be received as an input to the cascaded series of inverters. Each inverter includes at least one bioFET sensor. A frequency of the oscillating biosensor signal is based on the number of inverter stages, the size of the transistors used for the various inverters, and the operation of the bioFET sensors.

At block 1304, a digital count corresponding to a frequency of the oscillating biosensor signal is determined. A counting module may be used to determine the digital count that includes a counter and also uses a reference clock to provide a given number of cycles of the oscillating biosensor signal for one cycle of the reference clock. The reference clock may have a frequency between about 50 KHz and 150 KHz. In one example, a frequency of the reference clock is chosen to be at least 100 times lower, at least 1000 times lower, or at least 10,000 times lower than a frequency of the oscillating biosensor signal. The counter may use cascaded JK flip flops coupled together with the output of a given JK flip flop coupled to the clock input of the next JK flip flop.

Figure 14:
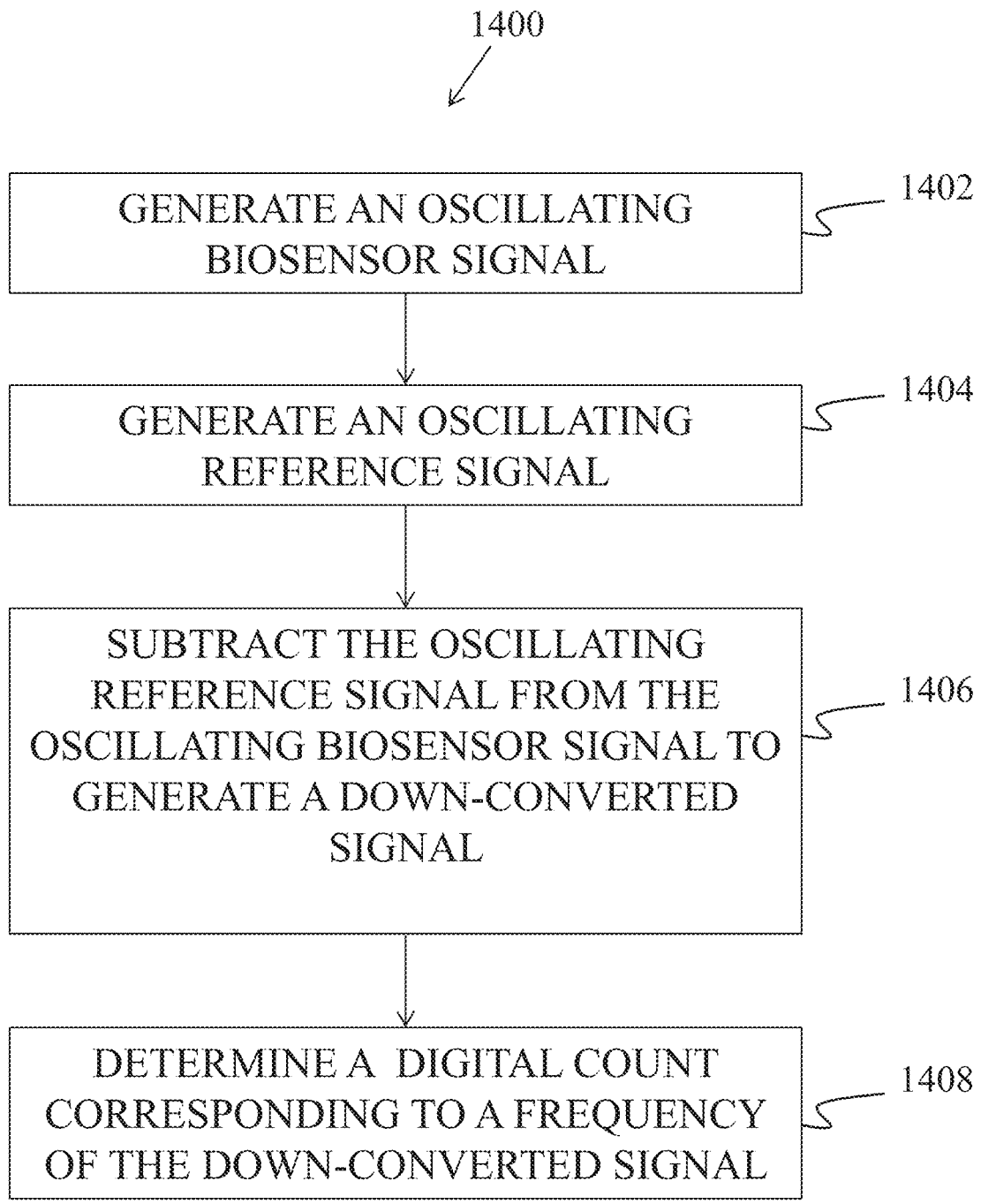
FIG. 14 illustrates a flow diagram of another exemplary method of measuring a sensing signal from one or more bioFET sensors, according to some embodiments.

Referring to FIG. 14, an example method 1400 is presented. Method 1400 may be performed by readout circuit 1000 to measure the sensor output of one or more bioFET sensors in a sensor array. Other operations relating to signal filtering or any other signal processing not illustrated in method 1400 may be performed either before, between, or after the illustrated operations of method 1400. The various operations of method 1400 may be performed in a different order than the one illustrated.

At block 1402, an oscillating biosensor signal is generated. The oscillating biosensor signal may be an output of a cascaded series of inverters, where the output is also fed back to be received as an input to the cascaded series of inverters. Each inverter includes at least one bioFET sensor. A frequency of the oscillating biosensor signal is based on the number of inverter stages, the size of the transistors used for the various inverters, and the operation of the bioFET sensors.

At block 1404, an oscillating reference signal is generated. The oscillating reference signal may be generated from another cascaded series of logic gates that is arranged similarly to those that generate the oscillating biosensor signal. In some embodiments, these cascaded series of logic gates do not include bioFET sensors. According to some embodiments, the oscillating reference signal has a frequency substantially equal to a frequency of the oscillating biosensor signal when no target analyte is bound to any of the bioFET sensors. In this way, any frequency change to the oscillating biosensor signal due to the presence of a target analyte provides a difference between the oscillating biosensor signal and the oscillating reference signal. The oscillating reference signal may have a frequency between about 150 MHz and about 250 MHz.

At block 1406, the oscillating reference signal is subtracted from the oscillating biosensor signal using a mixer component. The subtraction results in a down-converted signal output. The down-converted signal corresponds to a difference in the oscillation frequency between the oscillating biosensor signal and the oscillating reference signal. When the bioFET sensors are used as pH sensors, a change of 1 pH may be roughly equivalent to a 2 MHz shift in the frequency of the oscillating biosensor signal.

At block 1408, a digital count corresponding to a frequency of the down-converted signal is determined. A counting module may be used to determine the digital count that includes a counter and also uses a reference clock to provide a given number of cycles of the down-converted signal for one cycle of the reference clock. The reference clock may have a frequency between about 5 KHz and about 50 KHz. In one example, a frequency of the reference clock is chosen to be at least 100 times lower, at least 1000 times lower, or at least 10,000 times lower than a frequency of the down-converted signal. The counter may use cascaded JK flip flops coupled together with the output of a given JK flip flop coupled to the clock input of the next JK flip flop.

Chemistry, Biology, and Interface

The apparatus, systems, and methods described in this application can be used to monitor interactions between various entities. These interactions include biological and chemical reactions to detect target analytes in a test sample. As an example, reactions, including physical, chemical, biochemical, or biological transformations, can be monitored to detect generation of intermediates, byproducts, products, and combinations thereof. In addition, the apparatus, systems, and methods of the present disclosure can be used to detect these reactions in various assays as described herein, including, but not limited to, circulating tumor cell assays used in liquid biopsies and chelation assays to detect the presence of heavy metals and other environmental pollutants. Such assays and reactions can be monitored in a single format or in an array format to detect, e.g., multiple target analytes.

Biological Sensing Examples with Dual Gate Back-Side Sensing FET Sensor

Figure 15:
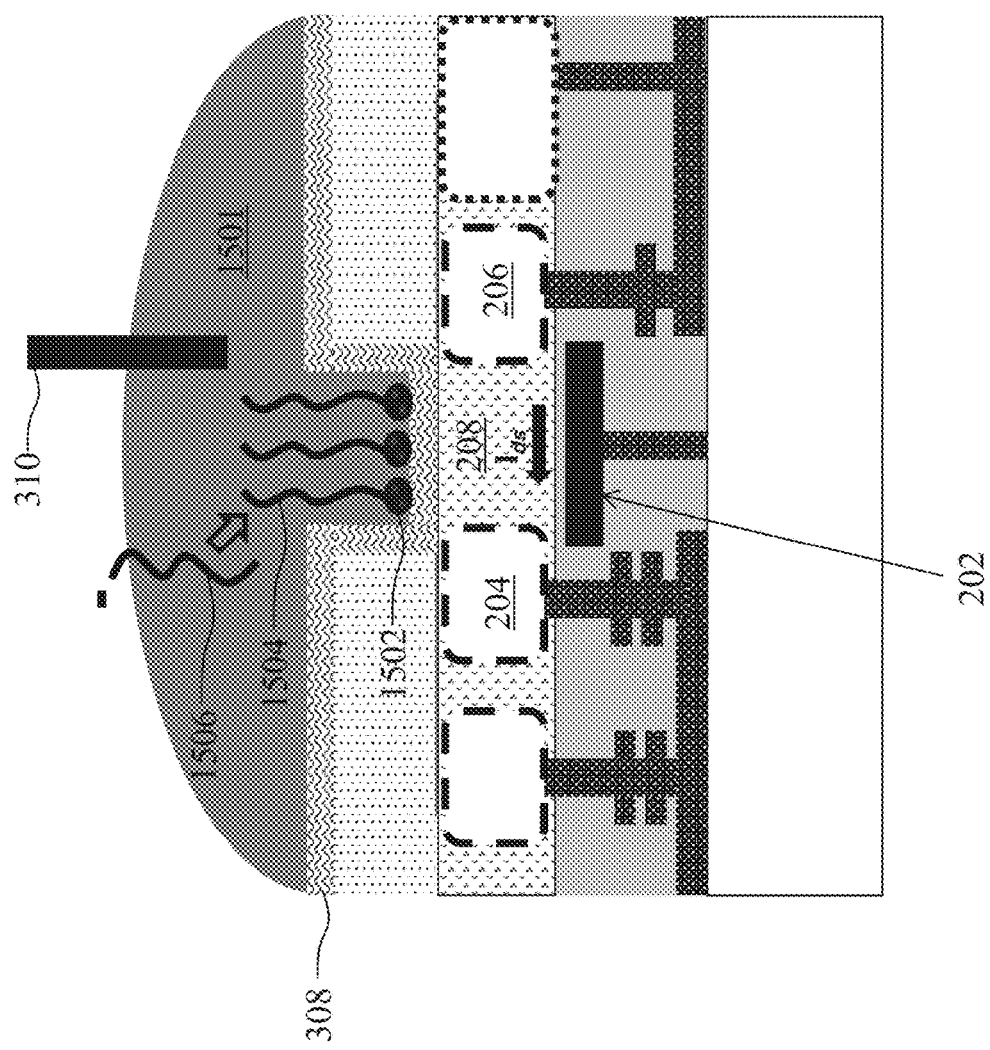
FIG. 15 illustrates a cross-sectional view of an exemplary dual gate back-side sensing bioFET detecting DNA, according to some embodiments.

Referring to FIG. 15, an example biosensing test is performed using the dual gate back-side sensing FET sensor described above in FIG. 3. Probe DNA 1504 (an example of a capture reagent) is bound to interface layer 308 via a linking molecule 1502. Linking molecule 1502 may have a reactive chemical group that binds to a portion of interface layer 308. An example of linking molecules include thiols. Linking molecules may also be formed via silanization of the surface of interface layer 308, or by exposing the surface of interface layer 308 to ammonia ($NH_3$) plasma, to form reactive $NH_2$ groups on the surface. The silanization process involves sequentially exposing the surface of interface layer 308 to different chemicals to build up covalently-bound molecules on the surface of interface layer 308, as would be generally understood by a person skilled in the relevant art. Probe DNA 1504 represents single stranded DNA. The dual gate back-side sensing FET sensor illustrated in FIG. 15 is one bioFET sensor within a sensor array that would exist on a chip, according to some embodiments.

Probe DNA 1504 may be immobilized on interface layer 308 prior to subjecting the FET sensor to fluid sample 1501. Fluid sample 1501 may be delivered to the surface of the FET sensor using a fluid delivery system. Fluid sample 1501 may include the matching single stranded DNA sequence 1506 that binds strongly to its matching probe DNA 1504. The binding of additional DNA increases the negative charge present on interface layer 308 and directly above channel region 208 of the FET sensor.

The DNA binding is illustrated conceptually in FIG. 16A. Here probe DNA having nucleic acid sequence TCGA binds to its complementary matched strand having nucleic acid sequence AGCT. Any unmatched sequences does not hybridize with the probe DNA sequences. The binding of the matching DNA increases the negative charge built up at the interface of interface layer 308. In the example illustrated in FIG. 16A, interface layer 308 is hafnium oxide.

FIG. 16B illustrates a shift in the threshold voltage of the dual gate back-side sensing FET sensor when matching DNA is bound to the surface of interface layer 308. Briefly, voltage may be applied to fluid gate 310 until the FET sensor "turns on" and current flows between drain region 206 and source region 204. In another example, voltage is applied to gate 202 to turn on the FET sensor while fluid gate 310 is biased at a given potential. When more negative charge is present at interface layer 308 due to complementary DNA binding, a higher voltage is required to form the conductive inversion layer within the channel region 208. Thus, according to some embodiments, a higher voltage may be applied to reference electrode 310, or gate 202, before the FET sensor conducts and $I_{ds}$ current flows. This difference in threshold voltage may be measured and used to determine not only the presence of the target matching DNA sequence, but also its concentration. It should be understood that a net positive accumulated charge at interface layer 308 would cause the threshold voltage to decrease rather than increase. Additionally, the change in threshold voltage will have the opposite sign for an n-channel FET as compared to a p-channel FET.

Figure 17:
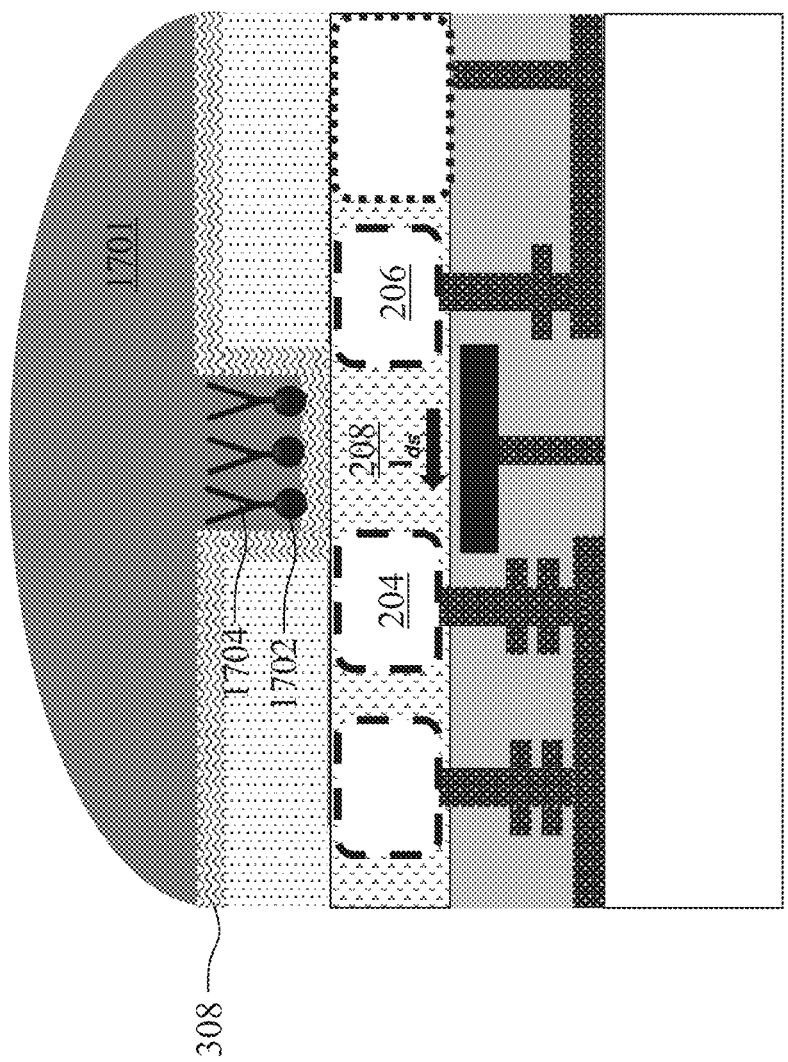
FIG. 17 illustrates a cross-sectional view of an exemplary dual gate back-side sensing bioFET having antibodies immobilized on its sensing layer, according to some embodiments.

Referring to FIG. 17, another example biosensing test is performed using the dual gate back-side sensing FET sensor. Probe antibodies 1704 (another example of capture reagents) are bound to interface layer 308 via linking molecules 1702. Linking molecules 1702 may have a reactive chemical group that binds to a portion of interface layer 308. A sample solution 1701 may be provided over probe antibodies 1704 to determine if the matching antigens are present within sample solution 1701.

Figure 18:
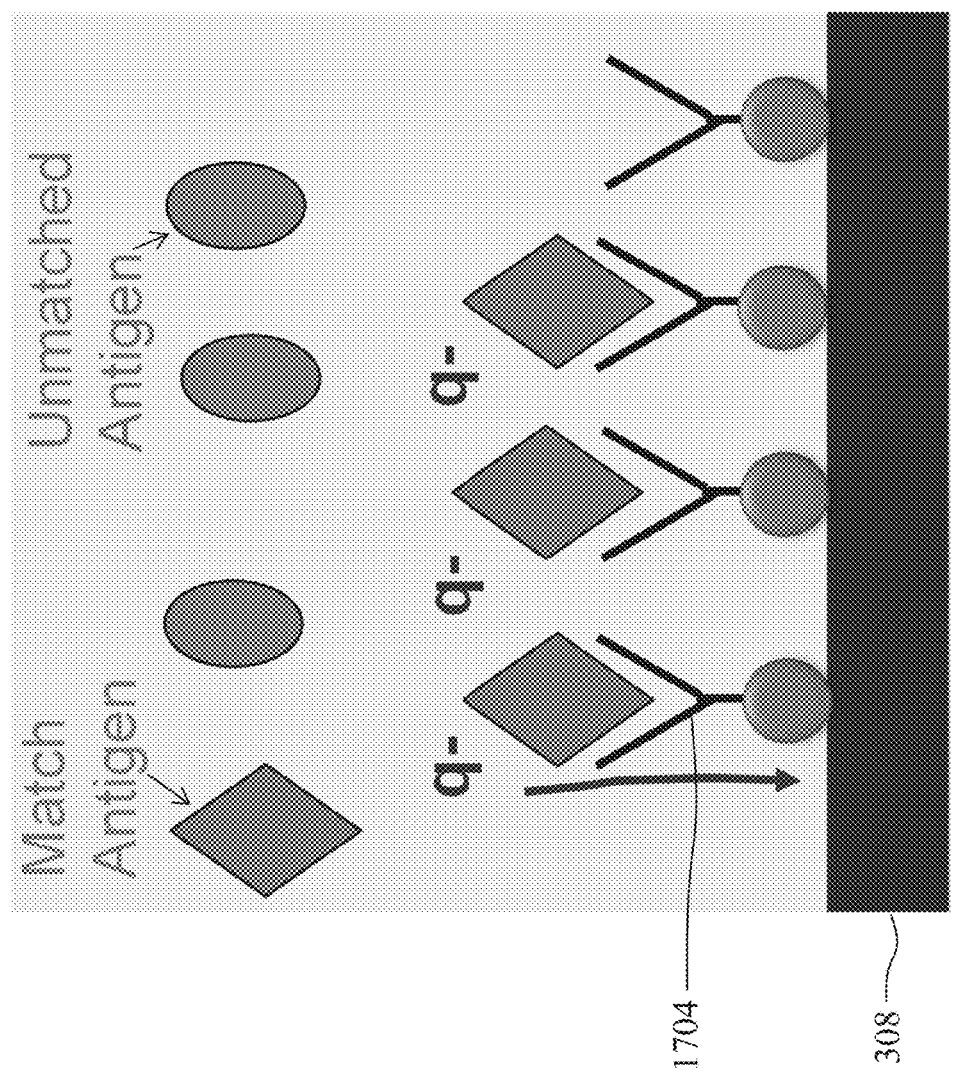
FIG. 18 illustrates binding mechanics of antigens and antibodies on a receptor surface, according to some embodiments.

Referring to FIG. 18, the binding process of matching antigens to probe antibodies 1704 is illustrated. Here, matching antigens will bind to the immobilized probe antibodies while unmatched antigens will not bind. Similar to the DNA hybridization process described above, the matching antigens will change the accumulated charge present at interface layer 308. The shift in threshold voltage due to the accumulated charge from matching antibodies binding to the probe antibodies is measured in substantially the same way as discussed above with reference to FIG. 16B.

Final Remarks

Described herein are embodiments of a readout circuit for use with bioFET sensors. According to some embodiments, a sensor readout circuit includes a plurality of logic gates coupled in cascade, a delay extractor, and a counting module. Each logic gate of the plurality of logic gates includes at least one bioFET sensor. The delay extractor is designed to generate a pulse-width signal based on a time difference between an output signal from the plurality of logic gates and a reference signal. The counting module is designed to receive the pulse-width signal and output a digital count corresponding to a width of the pulse-width signal.

According to some embodiments, a sensor readout circuit includes a plurality of inverters coupled in cascade, where each inverter includes at least one bioFET sensor. An output of the plurality of inverters is fed back to be received as an input to the plurality of inverters, thus forming a ring oscillator. The sensor readout circuit also includes a counting module designed to receive the output of the plurality of inverters and to output a digital count corresponding to a frequency of the output of the plurality of inverters.

According to some embodiments, a sensor readout circuit includes a plurality of inverters, a mixer, and a counting module. The plurality of inverters are coupled in cascade with each inverter having at least one bioFET sensor, and an output of the plurality of inverters is fed back to be received as an input to the plurality of inverters. The mixer receives the output of the plurality of inverters and an oscillating reference signal, and generates a down-converted signal corresponding to a difference in an oscillation frequency between the output of the plurality of inverters and the oscillating reference signal. The counting module is designed to receive the down-converted signal and to output a digital count corresponding to a frequency of the down-converted signal.

It is to be appreciated that the Detailed Description section, and not the Abstract of the Disclosure section, is intended to be used to interpret the claims. The Abstract of the Disclosure section may set forth one or more but not all exemplary embodiments of the present disclosure as contemplated by the inventor(s), and thus, is not intended to limit the present disclosure and the subjoined claims in any way.

It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments but should be defined in accordance with the subjoined claims and their equivalents.

What is claimed is:

1. A sensor readout circuit comprising:
a plurality of logic gates coupled in cascade, each logic gate comprising at least one bioFET sensor;
a delay extractor configured to generate a pulse-width signal based on a time difference between an output signal from the plurality of logic gates and a reference signal; and
a counting module configured to receive the pulse-width signal and output a digital count corresponding to a width of the pulse-width signal.

2. The sensor readout circuit of claim 1, further comprising a second plurality of logic gates coupled in cascade, wherein the reference signal is an output of the second plurality of logic gates.

3. The sensor readout circuit of claim 2, wherein an input of the plurality of logic gates coupled in cascade and an input of the second plurality of logic gates coupled in cascade are tied together to receive a same input signal.

4. The sensor readout circuit of claim 1, wherein the plurality of logic gates comprise a plurality of inverters.

5. The sensor readout circuit of claim 1, wherein the delay extractor comprises an XOR logic gate.

6. The sensor readout circuit of claim 1, wherein the counting module comprises:
an AND gate configured to receive the pulse-width signal and a clock signal and to output a pulse count signal; and
a digital counter configured to receive the pulse count signal and output the digital count.

7. The sensor readout circuit of claim 6, wherein the clock signal has a clock frequency between 800 MHz and 1.2 GHz.

8. The sensor readout circuit of claim 1, wherein the bioFET sensor is a dual-gate bioFET sensor.

9. The sensor readout circuit of claim 1, wherein the bioFET sensor in each logic gate comprises a functionalized surface exposed to a fluid within a microfluidic well or a microfluidic channel.

10. A sensor readout circuit comprising:
a plurality of inverters coupled in cascade, each inverter comprising at least one bioFET sensor, wherein an output of the plurality of inverters is fed back as an input to the plurality of inverters; and
a counting module configured to receive the output of the plurality of inverters and to output a digital count corresponding to a frequency of the output of the plurality of inverters.

11. The sensor readout circuit of claim 10, wherein the counting module comprises:
an AND gate configured to receive the output of the plurality of inverters and a clock signal and to output a count signal; and
a digital counter configured to receive the count signal and output the digital count.

12. The sensor readout circuit of claim 11, wherein the clock signal has a clock frequency between 50 kHz and 150 kHz.

13. The sensor readout circuit of claim 10, wherein the bioFET sensor is a dual-gate bioFET sensor.

14. The sensor readout circuit of claim 10, wherein the frequency of the output of the plurality of inverters is between 150 MHz and 250 MHz.

15. The sensor readout circuit of claim 10, wherein the bioFET sensor in each inverter includes a functionalized surface exposed to a fluid within a microfluidic well or a microfluidic channel.

16. A sensor readout circuit comprising:
a plurality of inverters coupled in cascade, each inverter comprising at least one bioFET sensor, wherein an output of the plurality of inverters is fed back as an input to the plurality of inverters;
a mixer configured to receive the output of the plurality of inverters and an oscillating reference signal and to generate a down-converted signal corresponding to a difference in an oscillation frequency between the output of the plurality of inverters and the oscillating reference signal; and a counting module configured to receive the down-converted signal and to output a digital count corresponding to a frequency of the down-converted signal.

17. The sensor readout circuit of claim 16, further comprising a second plurality of inverters coupled in cascade, wherein an output of the second plurality of inverters is fed back as an input to the second plurality of inverters, and wherein the oscillating reference signal is the output of the second plurality of inverters.

18. The sensor readout circuit of claim 16, wherein the mixer comprises a flip flop with a clock input coupled to the oscillating reference signal.

19. The sensor readout circuit of claim 16, wherein the counting module comprises:
    an AND gate configured to receive the down-converted signal and a clock signal and to output a count signal; and
    a digital counter configured to receive the count signal and output the digital count.

20. The sensor readout circuit of claim 19, wherein the clock signal has a frequency between 5 KHz and 50 KHz.

\* \* \* \* \*